(12) United States Patent
Sachar et al.

(10) Patent No.: US 9,707,071 B2
(45) Date of Patent: Jul. 18, 2017

(54) PERCUTANEOUS TRANSLUMINAL ANGIOPLASTY DEVICE WITH INTEGRAL EMBOLIC FILTER

(75) Inventors: Ravish Sachar, Raleigh, NC (US); Udayan Patel, San Jose, CA (US)

(73) Assignee: Contego Medical LLC, Raleigh, NC (US)

( * ) Notice: Subject to any disclaimer, the term of this patent is extended or adjusted under 35 U.S.C. 154(b) by 0 days.

(21) Appl. No.: 11/763,118

(22) Filed: Jun. 14, 2007

(65) Prior Publication Data

US 2007/0299466 A1     Dec. 27, 2007

Related U.S. Application Data

(63) Continuation-in-part of application No. 10/997,803, filed on Nov. 24, 2004, now Pat. No. 8,403,976.

(60) Provisional application No. 60/813,395, filed on Jun. 14, 2006.

(51) Int. Cl.
| | |
|---|---|
| *A61M 29/00* | (2006.01) |
| *A61F 2/00* | (2006.01) |
| *A61F 2/01* | (2006.01) |
| *A61M 25/10* | (2013.01) |

(52) U.S. Cl.
CPC .......... *A61F 2/013* (2013.01); *A61M 25/104* (2013.01); *A61F 2002/018* (2013.01); *A61F 2230/0006* (2013.01); *A61F 2230/008* (2013.01)

(58) Field of Classification Search
CPC .... A61F 2/01; A61F 2/06; A61F 2/013; A61F 2002/011; A61F 2002/016; A61F 2002/018

USPC .......... 606/200, 113, 114; 623/1.15
See application file for complete search history.

(56) References Cited

U.S. PATENT DOCUMENTS

| | | |
|---|---|---|
| 4,723,549 A | 2/1988 | Wholey et al. |
| 5,053,008 A | 10/1991 | Bajaj |
| 5,108,419 A | 4/1992 | Reger et al. |
| 5,456,667 A | 10/1995 | Ham et al. |

(Continued)

FOREIGN PATENT DOCUMENTS

| | | |
|---|---|---|
| DE | 20 2005 022 063.9 | 11/2005 |
| DE | 202005022063 U1 | 3/2013 |

(Continued)

OTHER PUBLICATIONS

"Mounted," *American Webster Dictionary* http://dictionary.reference.com/browse/mounted, Jan. 28, 2007.

(Continued)

*Primary Examiner* — Anh Dang
(74) *Attorney, Agent, or Firm* — Meunier Carlin & Curfman LLC

(57) ABSTRACT

A percutaneous transluminal angioplasty device includes an embolic filter mounted to the catheter shaft at a location distal to the angioplasty balloon. Thus the filter is downstream from the blockage and is properly positioned to capture embolic particles that may be set loose into the blood stream as the angioplasty procedure is performed. The embolic filter is normally collapsed against the catheter shaft to facilitate introduction and withdrawal of the device to and from the operative site. Once the angioplasty balloon is properly positioned, however, means operatively associated with the embolic filter are actuated to erect the filter to position a filter mesh across the lumen of the vessel.

19 Claims, 22 Drawing Sheets

(56) References Cited

U.S. PATENT DOCUMENTS

| | | | |
|---|---|---|---|
| 5,913,895 A | 6/1999 | Burpee et al. | |
| 5,954,745 A | 9/1999 | Gertler et al. | |
| 6,001,118 A | 12/1999 | Daniel et al. | |
| 6,042,598 A | 3/2000 | Tsugita et al. | |
| 6,051,014 A | 4/2000 | Jang | |
| 6,168,579 B1 | 1/2001 | Tsugita | |
| 6,179,859 B1 | 1/2001 | Bates et al. | |
| 6,325,815 B1 | 12/2001 | Kusleika et al. | |
| 6,344,049 B1 | 2/2002 | Levinson et al. | |
| 6,355,051 B1 | 3/2002 | Sisskind et al. | |
| 6,371,970 B1 | 4/2002 | Khosravi et al. | |
| 6,391,044 B1 | 5/2002 | Yadav et al. | |
| 6,485,502 B2 | 11/2002 | Don et al. | |
| 6,511,496 B1 | 1/2003 | Huter et al. | |
| 6,511,503 B1 | 1/2003 | Burkett et al. | |
| 6,524,303 B1 | 2/2003 | Garibaldi | |
| 6,537,297 B2 | 3/2003 | Tsugita et al. | |
| 6,540,722 B1 * | 4/2003 | Boyle et al. | 604/106 |
| 6,592,606 B2 | 7/2003 | Huter et al. | |
| 6,596,011 B2 | 7/2003 | Johnson et al. | |
| 6,607,506 B2 | 8/2003 | Kletschka | |
| 6,635,084 B2 | 10/2003 | Israel et al. | |
| 6,638,294 B1 | 10/2003 | Palmer | |
| 6,652,557 B1 | 11/2003 | Macdonald | |
| 6,656,203 B2 | 12/2003 | Roth et al. | |
| 6,656,351 B2 | 12/2003 | Boyle | |
| 6,663,650 B2 | 12/2003 | Sepetka et al. | |
| 6,682,543 B2 | 1/2004 | Barbut et al. | |
| 6,702,834 B1 | 3/2004 | Boylan et al. | |
| 6,866,677 B2 | 3/2005 | Douk et al. | |
| 6,939,373 B2 | 9/2005 | Gomez et al. | |
| 6,964,673 B2 | 11/2005 | Tsugita et al. | |
| 6,969,396 B2 | 11/2005 | Krolik et al. | |
| 6,978,174 B2 | 12/2005 | Gelfand et al. | |
| 6,991,641 B2 | 1/2006 | Diaz et al. | |
| 6,994,718 B2 | 2/2006 | Groothuis et al. | |
| 7,044,958 B2 | 5/2006 | Douk et al. | |
| 7,083,633 B2 | 8/2006 | Morrill et al. | |
| 7,094,249 B1 | 8/2006 | Broome et al. | |
| 7,097,651 B2 | 8/2006 | Harrison et al. | |
| 7,137,991 B2 | 11/2006 | Fedie | |
| 7,150,756 B2 | 12/2006 | Levinson et al. | |
| 7,163,549 B2 | 1/2007 | Crank et al. | |
| 7,241,305 B2 | 7/2007 | Ladd | |
| 7,338,510 B2 | 3/2008 | Boylan et al. | |
| 7,481,823 B2 | 1/2009 | Broome et al. | |
| 7,780,696 B2 * | 8/2010 | Daniel et al. | 606/200 |
| 7,935,075 B2 | 5/2011 | Tockman et al. | |
| 8,150,520 B2 | 4/2012 | Demarais et al. | |
| 8,303,617 B2 | 11/2012 | Brady et al. | |
| 8,372,108 B2 | 2/2013 | Lashinski | |
| 8,403,976 B2 | 3/2013 | Sachar et al. | |
| 8,409,240 B2 | 4/2013 | Tripp et al. | |
| 8,518,073 B2 | 8/2013 | Lashinski | |
| 8,603,131 B2 | 12/2013 | Gilson et al. | |
| 8,657,849 B2 | 2/2014 | Parker | |
| 8,679,148 B2 | 3/2014 | McGuckin | |
| 8,740,930 B2 | 6/2014 | Goodwin | |
| 8,758,424 B2 | 6/2014 | Sachar et al. | |
| 8,852,225 B2 | 10/2014 | Shu | |
| 8,945,169 B2 | 2/2015 | Pal | |
| 8,974,490 B2 | 3/2015 | Jonsson | |
| 9,017,364 B2 | 4/2015 | Fifer | |
| 9,023,077 B2 | 5/2015 | Cully et al. | |
| 2001/0012951 A1 | 8/2001 | Bates et al. | |
| 2002/0156457 A1 | 10/2002 | Fisher | |
| 2003/0004536 A1 | 1/2003 | Boylan et al. | |
| 2003/0055480 A1 | 3/2003 | Fischell et al. | |
| 2003/0060843 A1 | 3/2003 | Boucher | |
| 2003/0065354 A1 * | 4/2003 | Boyle et al. | 606/200 |
| 2003/0083736 A1 | 5/2003 | Brown et al. | |
| 2003/0093106 A1 | 5/2003 | Brady et al. | |
| 2003/0139764 A1 * | 7/2003 | Levinson et al. | 606/200 |
| 2003/0167084 A1 | 9/2003 | Orlowski | |
| 2003/0176884 A1 | 9/2003 | Berrada et al. | |
| 2003/0212361 A1 | 11/2003 | Boyle et al. | |
| 2003/0216792 A1 | 11/2003 | Levin et al. | |
| 2003/0220665 A1 | 11/2003 | Eskuri et al. | |
| 2003/0225435 A1 * | 12/2003 | Huter et al. | 606/200 |
| 2004/0054322 A1 | 3/2004 | Vargas | |
| 2004/0122466 A1 | 6/2004 | Bales | |
| 2004/0158280 A1 | 8/2004 | Morris et al. | |
| 2004/0167564 A1 | 8/2004 | Fedie | |
| 2004/0172128 A1 | 9/2004 | Hong et al. | |
| 2004/0260387 A1 | 12/2004 | Regala et al. | |
| 2005/0015111 A1 | 1/2005 | McGuckin et al. | |
| 2005/0038468 A1 * | 2/2005 | Panetta et al. | 606/200 |
| 2005/0119668 A1 | 6/2005 | Teague et al. | |
| 2005/0228438 A1 | 10/2005 | Sachar et al. | |
| 2005/0288730 A1 | 12/2005 | Deem et al. | |
| 2006/0015139 A1 | 1/2006 | Tsugita et al. | |
| 2006/0041277 A1 | 2/2006 | Deem et al. | |
| 2006/0100658 A1 | 5/2006 | Obana et al. | |
| 2006/0129130 A1 | 6/2006 | Tal et al. | |
| 2006/0129180 A1 | 6/2006 | Tsugita et al. | |
| 2006/0142801 A1 | 6/2006 | Demarais et al. | |
| 2006/0235474 A1 | 10/2006 | Demarais | |
| 2007/0043306 A1 | 2/2007 | Olson | |
| 2007/0061418 A1 | 3/2007 | Berg | |
| 2007/0167975 A1 | 7/2007 | Boyle et al. | |
| 2007/0299466 A1 | 12/2007 | Sachar et al. | |
| 2008/0097399 A1 | 4/2008 | Sachar et al. | |
| 2010/0010534 A1 | 1/2010 | Mujkanovic | |
| 2010/0106182 A1 | 4/2010 | Patel et al. | |
| 2011/0004291 A1 | 1/2011 | Davis et al. | |
| 2011/0071619 A1 | 3/2011 | Bliss et al. | |
| 2011/0137399 A1 | 6/2011 | Chomas et al. | |
| 2012/0330402 A1 | 12/2012 | Vad et al. | |
| 2013/0031087 A1 | 1/2013 | Kropitz et al. | |
| 2013/0310871 A1 | 1/2013 | Kropitz et al. | |
| 2013/0226225 A1 | 8/2013 | Sachar et al. | |
| 2014/0052170 A1 | 2/2014 | Heuser et al. | |
| 2014/0135661 A1 | 5/2014 | Garrison et al. | |
| 2014/0214067 A1 | 7/2014 | Sachar et al. | |
| 2014/0277383 A1 | 9/2014 | Sachar et al. | |
| 2015/0018928 A1 | 1/2015 | Sachar et al. | |
| 2015/0025567 A1 | 1/2015 | Ren et al. | |
| 2015/0133918 A1 | 5/2015 | Sachar | |

FOREIGN PATENT DOCUMENTS

| | | |
|---|---|---|
| EP | 05852233.5 | 11/2005 |
| EP | 1951147 A2 | 8/2008 |
| HK | 09101129.3 | 11/2005 |
| JP | 2002-336261 A | 11/2002 |
| JP | 2008-542291 | 11/2005 |
| JP | 2013-049398 | 3/2013 |
| JP | 2013-154183 A | 8/2013 |
| WO | WO-2004/096089 A2 | 11/2004 |
| WO | WO-2005/004968 A1 | 1/2005 |
| WO | WO 2007/061418 | 5/2007 |
| WO | WO-2007/061418 A2 | 5/2007 |
| WO | WO-2009/151761 A1 | 12/2009 |
| WO | PCT/US2013/072232 | 11/2013 |
| WO | PCT/US2014/021850 | 3/2014 |
| WO | PCT/US2014/029342 | 3/2014 |
| WO | WO-2014/085590 A1 | 6/2014 |
| WO | WO-2014/144787 A1 | 9/2014 |
| WO | WO-2014/150013 A1 | 9/2014 |
| WO | WO 2015/070147 | 5/2015 |

OTHER PUBLICATIONS

PCT/US05/042826 International Search Report and Written Opinion, Jun. 28, 2007, Protection Device, LLC.

Baim, Donald S.; Wahr, Dennis; George, Barry et al., Randomized Trial of a Distal Embolic Protection Device During Percutaneous Intervention of Saphenous Vein Aorto-Coronary Bypass Grafts, Circulation, Mar. 19, 2002, vol. 105, pp. 1285-1290.

International Application Serial No. PCT/US09/40202 International Search Report and Written Opinion mailed Nov. 5, 2009.

U.S. Appl. No. 61/730,213, filed Nov. 27, 2012, Sachar (Contego Medical, LLC).

(56) References Cited

OTHER PUBLICATIONS

U.S. Appl. No. 61/794,877, filed Mar. 15, 2013, Sachar (Contego Medical, LLC).
U.S. Appl. No. 14/091,903, filed Nov. 27, 2013, Sachar (Contego Medical, LLC).
U.S. Appl. No. 61/794,924, filed Mar. 15, 2013, Sachar (Contego Medical, LLC).
U.S. Appl. No. 14/213,668, filed Mar. 14, 2014, Sachar (Contego Medical, LLC).
U.S. Appl. No. 61/901,734, filed Nov. 8, 2013, Sachar (Contego Medical, LLC).
International Search Report and Written Opinion issued Jul. 21, 2014 for International Patent Application No. PCT/US14/21850, which was filed on Mar. 7, 2014 (Inventor—Sachar; Applicant—Contego Medical, LLC) (pp. 1-9).
International Search Report and Written Opinion issued Aug. 19, 2014 for International Patent Application No. PCT/US2014/029342, which was filed on Mar. 14, 2014 (Inventor—Sachar; Applicant—Contego Medical, LLC) (pp. 1-6).
Issue Notification issued Jun. 5, 2014 for U.S. Appl. No. 13/850,782, filed Mar. 26, 2013 and published as U.S. 2013/0226225 on Aug. 29, 2013 (Inventor—Sachar; Applicant—Contego Medical, LLC) (p. 1).
Final Office Action issued Aug. 21, 2014 for U.S. Appl. No. 12/604,236, filed Oct. 22, 2009 and published as U.S. 2010/0106182 on Apr. 29, 2010 (Inventor—Patel; Applicant—Contego Medical, LLC) (pp. 1-11).
Kumar et al. "Effects of Design Parameters on the Radial Force of Percutaneous Aortic Valve Stents," Cardiovasc Revasc Med. Apr.-Jun. 2010;11(2):101-4.
Response to Final Office Action filed Dec. 29, 2014 for U.S. Appl. No. 12/604,236, filed Oct. 22, 2009 and published as U.S. 2010/0106182 on Apr. 29, 2010 (Inventor—Patel; Applicant—Contego Medical, LLC) (pp. 1-17).
Non-Final Office Action issued Feb. 2, 2015 for U.S. Appl. No. 13/838,523, filed Mar. 15, 2013 and published as U.S. 2013/0310871 on Nov. 21, 2013 (Inventor—Sachar; Applicant—Contego Medical, LLC) (pp. 1-9).
Non-Final Office Action issued Mar. 5, 2015 for U.S. Appl. No. 14/213,668, filed Mar. 14, 2014 and published as U.S. 2014/0277383 on Sep. 18, 2014 (Inventor—Sachar; Applicant—Contego Medical, LLC) (pp. 1-13).
International Search Report and Written Opinion issued Feb. 23, 2015 for International Patent Application No. PCT/US2014/064817, which was filed on Nov. 10, 2014 and published as WO 2015/070147 on May 14, 2015 (Inventor—Sachar; Applicant—Contego Medical, LLC) (pp. 1-6).
Ansel, G.M., et al, "Carotid stenting with embolic protection: evolutionary advances," Expert Rev Med Devices (Jul. 2008) 5(4):427-436.
Bijuklic, K., "The PROFI study (Prevention of Cerebral Embolization by Proximal Balloon Occlusion Compared to Filter Protection During Carotid Artery Stenting): a prospective randomized trial," J Am Coll Cardiel (Apr. 10, 2012) 59(15): 1383-1389.
Charalambous, N., et al, "Reduction of cerebral embolization in carotid angioplasty: an in-vitro experiment comparing 2 cerebral protection devices," J Endovasc Ther (Apr. 2009) 16(2): 161-167.
Eskandari, M.K., "Cerebral embolic protection," Semin Vase Surg (Jun. 2005) 18(2):95-100.
Karada, K., et al, ""Significance of combining distal filter protection and a guiding catheter with temporary balloon occlusion for carotid artery stenting: clinical results and evaluation of debris capture,"" Ann Vase Surg (Oct. 2012) 26(7): 929-936.
International Search Report and Wirtten Opinion issued Dec. 22, 2015 for Application No. PCT/US2015/052360, 9 pages.
Kasirajan, K., et al, "Filter devices for cerebral protection during carotid angioplasty and stenting," J Endovasc Ther (Dec. 2003) 10(6):1039-1045.

Macdonald, S. (2006). Is there any evidence that cerebral protection is beneficial?: Experimental data. Journal of Cardiovascular Surgery, 47(2), 127.
Mathias, K., "Carotid artery stenting with filters," J Cardiovasc Surg (Torino) (Feb. 2013) 54(2): 33-39.
Muller-Hulsbeck, S., et al, "In vitro comparison of four cerebral protection filters for preventing human plaque embolization during carotid interventions," J Endovasc Ther (Dec. 2002) 9(6):793-802.
Ohki, T, ""Critical analysis of distal protection devices,"" Semin Vase Surg (Dec. 2003) 16(4):317-325.
Order, B.M., et al, "Comparison of 4 cerebral protection filters for carotid angioplasty: an in vitro experiment focusing on carotid anatomy," J Endovasc Ther (Apr. 2004) 11(2):211-218.
Sharma, Samin K. "Selection of Guide Wires and Specialty Devices," Apr. 2014, 93 pages (also available on-line at http://cccsymposium.org/2014-interventional_card-ppts/06-10-14_12-30_sharma.pdf).
Extended European Search Report issued in Application No. EP 13857790.3, issued Jun. 9, 2016, 10 pages.
International Preliminary Report on Patentability issued Oct. 12, 2010 for International Patent Application No. PCT/US09/040202, which was filed on Apr. 10, 2009 and published as WO 2009/151761 on Dec. 17, 2009 (Inventor—Sachar; Applicant—Contego Medical, LLC) (pp. 1-5).
International Preliminary Report on Patentability issued May 27, 2008 for International Patent Application No. PCT/US05/042826, Which was filed on Nov. 26, 2005 and published as WO 2007/061418 on May 31, 2007 (Inventor—Sachar; Applicant—Contego Medical, LLC) (pp. 1-4).
International Search Report and Written Opinion issued Feb. 18, 2014 for International Patent Application No. PCT/US2013/072232, which was filed on Nov. 27, 2013 (Inventor—Sachar; Applicant—Contego Medical, LLC) (pp. 1-9).
Restriction Requirement issued Apr. 12, 2007 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-6).
Response to Restriction Requirement filed Jun. 12, 2007 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-13).
Non-Final Office Action issued Aug. 23, 2007 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).
Response to Non-Final Office Action filed Nov. 19, 2007 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-18).
Final Office Action issued Feb. 5, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1- 9).
Pre-Appeal Brief Request and Notice of Appeal filed Apr. 23, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-5).
Notice of Panel Decision from Pre-Appeal Brief Review issued Jun. 5, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-2).
Amendment and Request for Continued Examination filed Aug. 5, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-10).
Non-Final Office Action issued Oct. 29, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).
Non-Final Office Action issued Feb. 10, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).

(56) References Cited

OTHER PUBLICATIONS

Examiner Interview Summary issued Mar. 11, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-4).
Response to Non-Final Office Action filed Mar. 30, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-17).
Applicant Summary of Interview with Examiner filed Mar. 31, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-3).
Final Office Action issued Jun. 16, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).
Response After Final Office Action filed Aug. 12, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-11).
Final Office Action issued Sep. 2, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-10).
Examiner Interview Summary issued Nov. 20, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-4).
Applicant Summary of Interview with Examiner filed Mar. 1, 2010 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).
Response to Final Office Action filed Mar. 2, 2010 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-11).
Final Office Action issued Mar. 17, 2010 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-10).
Amendment and Request for Continued Examination filed Sep. 17, 2010 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-13).
Non-Final Office Action issued May 19, 2011 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-9).
Response to Non-Final Office Action filed Jun. 23, 2011 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-22).
Final Office Action issued Sep. 27, 2011 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-13).
Response After Final Office Action filed Nov. 29, 2011 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-19).
Advisory Action issued Jan. 11, 2012 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-3).
Response and Request for Continued Examination filed Feb. 27, 2012 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-11).
Applicant-Initiated Interview Summary issued Jan. 2, 2013 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-3).
Notice of Allowance issued Feb. 20, 2013 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-10).
Examiner-Initiated Interview Summary issued Feb. 20, 2013 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-1).
Issue Notification issued Mar. 6, 2013 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-1).
Examiner-Initiated Interview Summary issued Oct. 9, 2013 for U.S. Appl. No. 13/850,782, filed Mar. 26, 2013 and published as U.S. 2013/0226225 on Aug. 29, 2013 (Inventor—Sachar; Applicant—Contego Medical, LLC) (pp. 1-1).
Notice of Allowance issued Oct. 9, 2013 for U.S. Appl No. 13/850,782, filed Mar. 26, 2013 and published as U.S. 2013/0226225 on Aug. 29, 2013 (Inventor—Sachar; Applicant—Contego Medical, LLC) (pp. 1-14).
Amendment and Response filed Mar. 27, 2014 for U.S. Appl. No. 13/850,782, filed Mar. 26, 2013 and published as U.S. 2013/0226225 on Aug. 29, 2013 (Inventor—Sachar; Applicant—Contego Medical, LLC) (pp. 1-6).
Response to Amendment issued Apr. 1, 2014 for U.S. Appl. No. 13/850,782, filed Mar. 26, 2013 and published as U.S. 2013/0226225 on Aug. 29, 2013 (Inventor—Sachar; Applicant—Contego Medical, LLC) (pp. 1-2).
Non-Final Office Action issued Apr. 13, 2011 for U.S. Appl. No. 12/604,236, filed Oct. 22, 2009 and published as U.S. 2010/0106182 on Apr. 29, 2010 (Inventor—Patel; Applicant—Contego Medical, LLC) (pp. 1-5).
Response to Non-Final Office Action filed Sep. 13, 2011 for U.S. Appl. No. 12/604,236, filed Oct. 22, 2009 and published as U.S. 2010/0106182 on Apr. 29, 2010 (Inventor—Patel; Applicant—Contego Medical, LLC) (pp. 1-27).
Final Office Action issued Nov. 21, 2011 for U.S. Appl. No. 12/604,236, filed Oct. 22, 2009 and published as U.S. 2010/0106182 on Apr. 29, 2010 (Inventor—Patel; Applicant—Contego Medical, LLC) (pp. 1-12).
Response and Request for Continued Examination filed Mar. 21, 2012 for U.S. Appl. No. 12/604,236, filed Oct. 22, 2009 and published as U.S. 2010/0106182 on Apr. 29, 2010 (Inventor—Patel; Applicant—Contego Medical, LLC) (pp. 1-17).
Non-Final Office Action issued Jan. 22, 2014 for U.S. Appl. No. 12/604,236, filed Oct. 22, 2009 and published as U.S. 2010/0106182 on Apr. 29, 2010 (Inventor—Patel; Applicant—Contego Medical, LLC) (pp. 1-9).
Preliminary Amendment filed Mar. 17, 2014 for U.S. Appl. No. 14/091,903, filed Nov. 27, 2013 (Inventor—Sachar; Applicant—Contego Medical, LLC) (pp. 1-3).
Amendment and Response to Non-Final Office Action filed Apr. 22, 2014 for U.S. Appl. No. 12/604,236, filed Oct. 22, 2009 and published as U.S. 2010/0106182 on Apr. 29, 2010 (Inventor—Patel; Applicant—Contego Medical, LLC) (pp. 1-14).
Amendment and Response to Notice of Incomplete Reply filed Apr. 21, 2014 for U.S. Appl. No. 14/091,903, filed Nov. 27, 2013 (Inventor—Sachar; Applicant—Contego Medical, LLC) (pp. 1-3).
European Search Report issued Oct. 7, 2011 for European Patent Application No. 05852233.5, which was filed on Nov. 26, 2005 and published as EP 1951147 on Aug. 6, 2008 (Inventor—Sachar; Application—Contego Medical, LLC) (pp. 1-7).

* cited by examiner

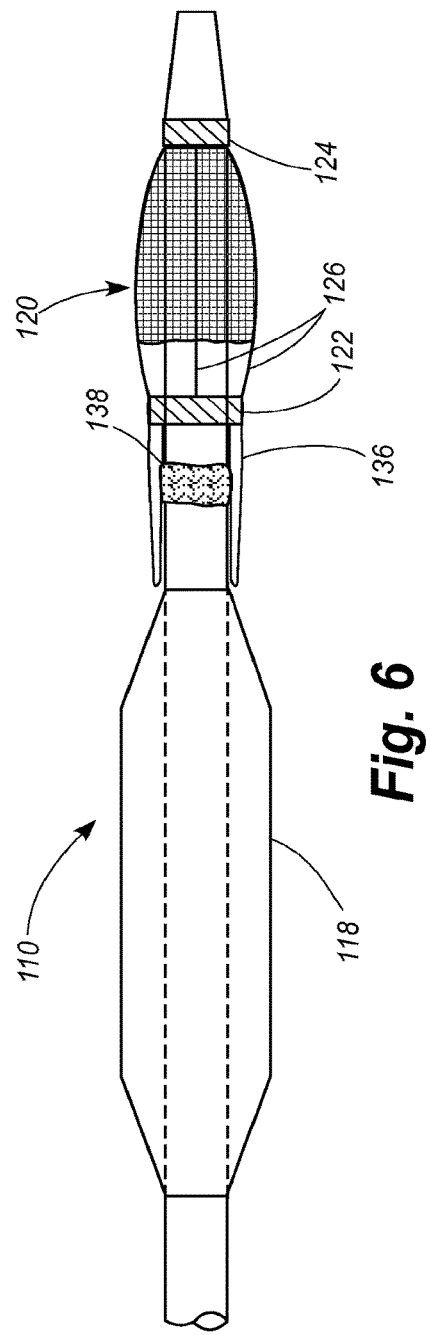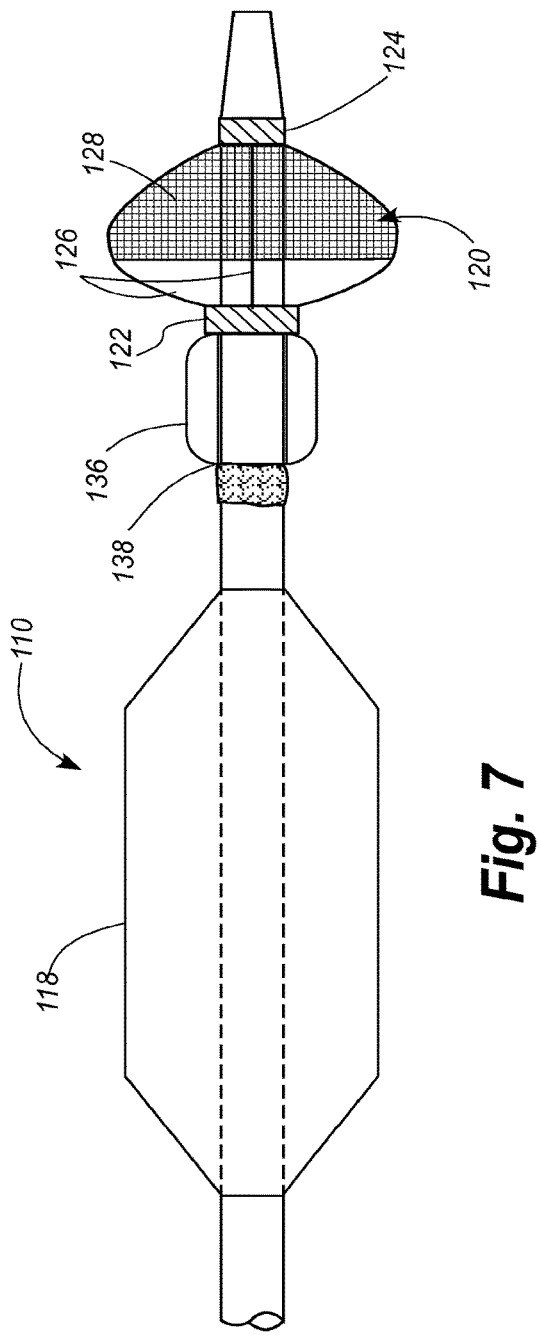

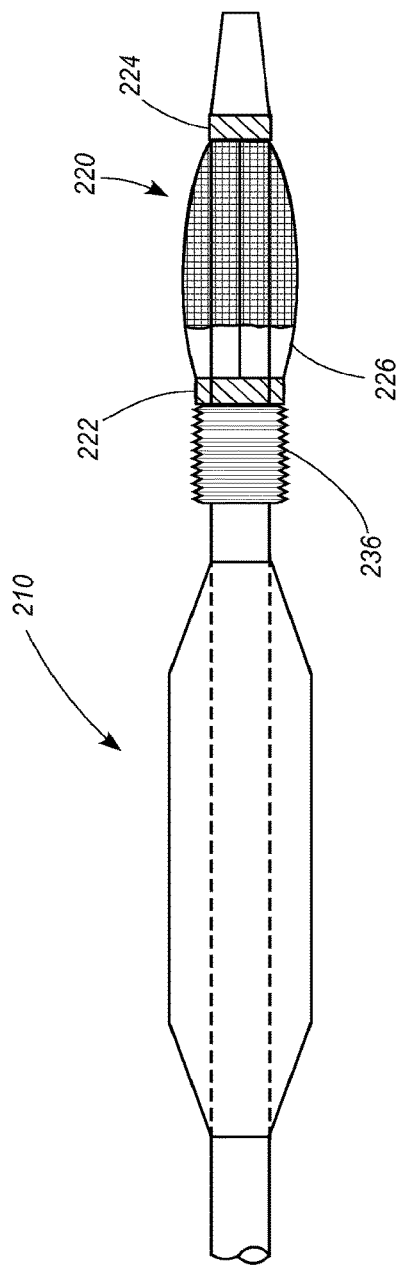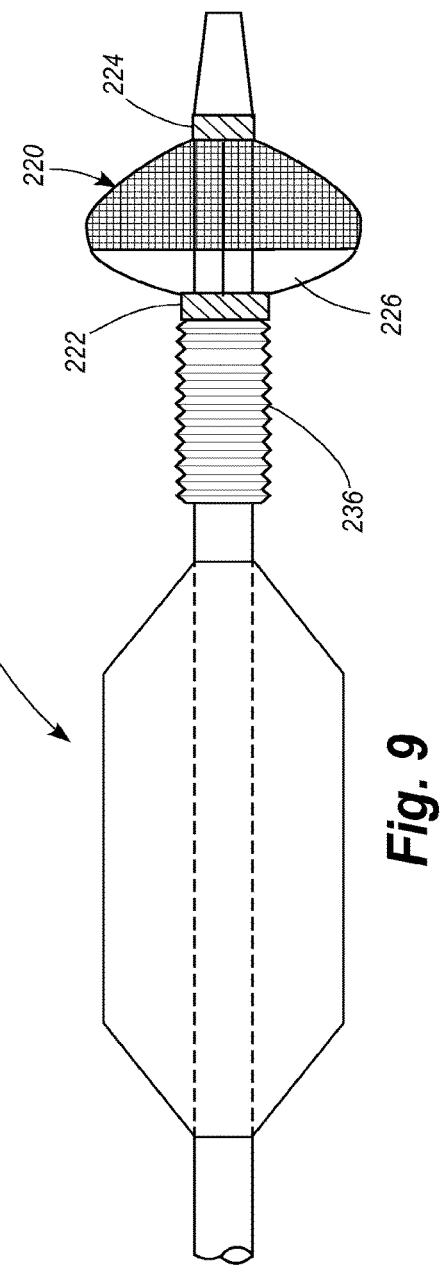

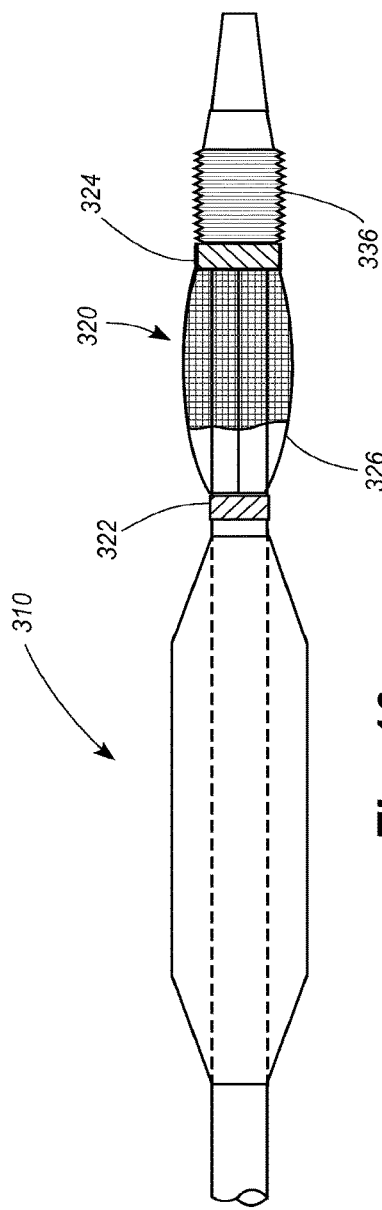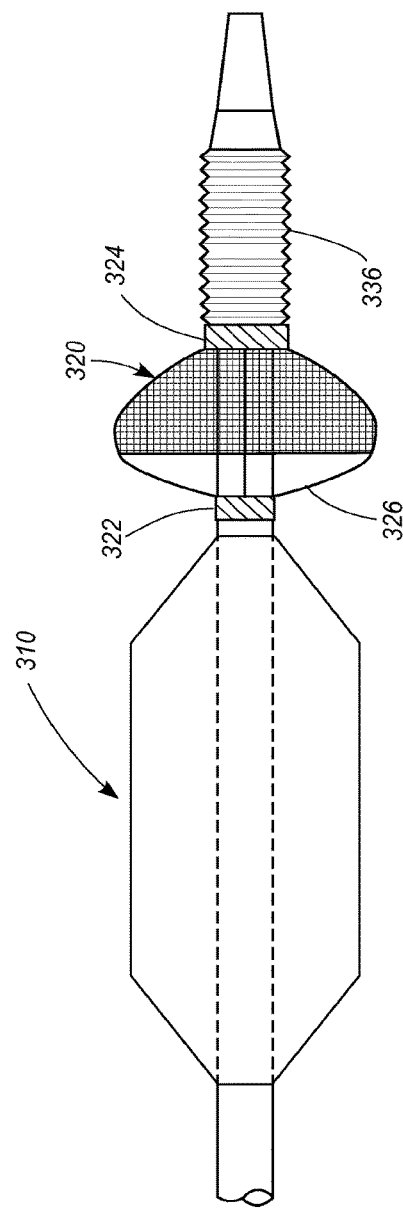

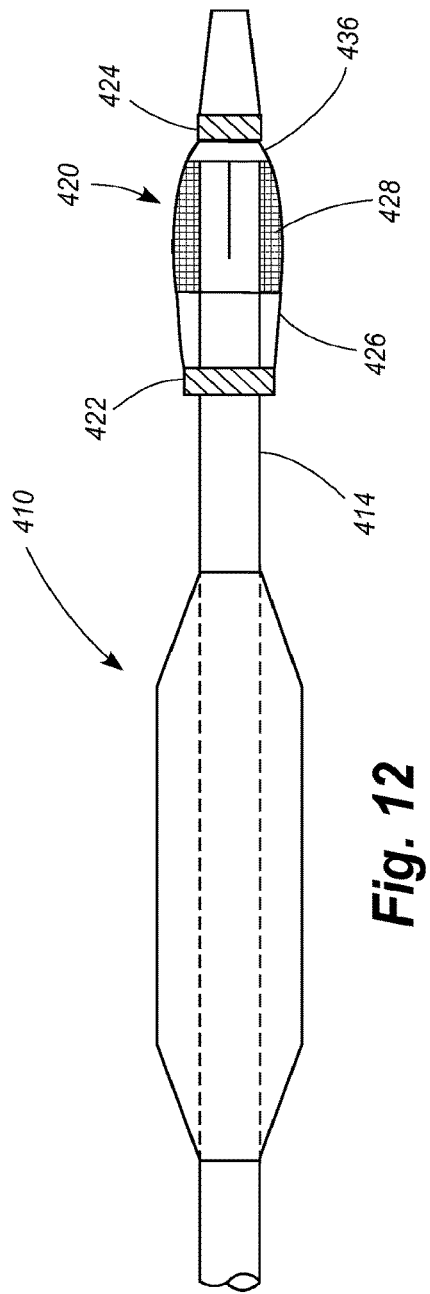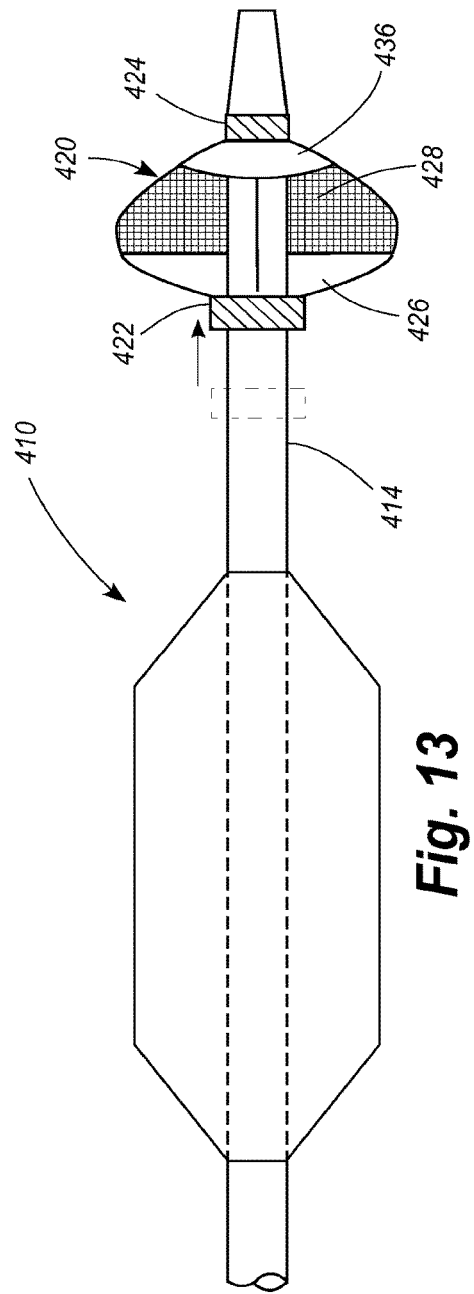

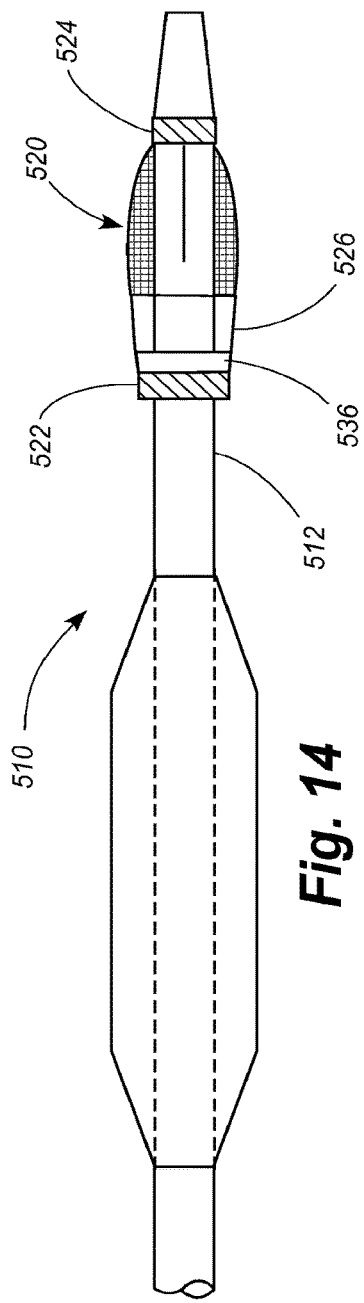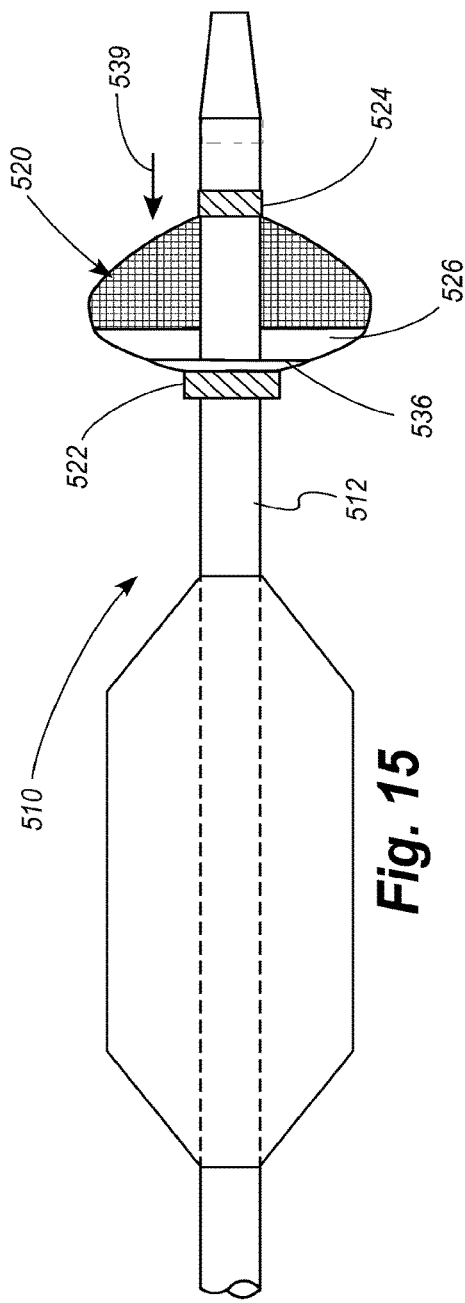

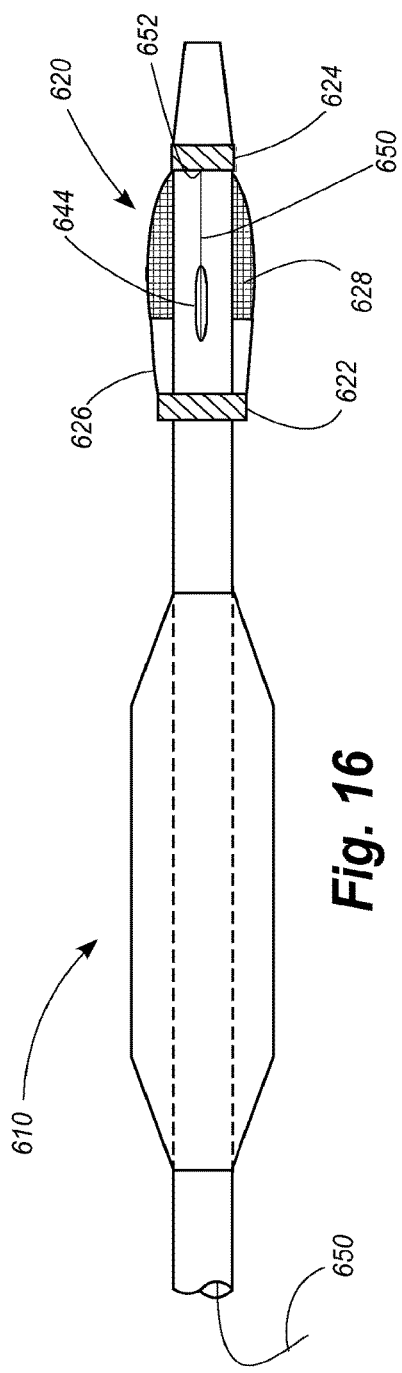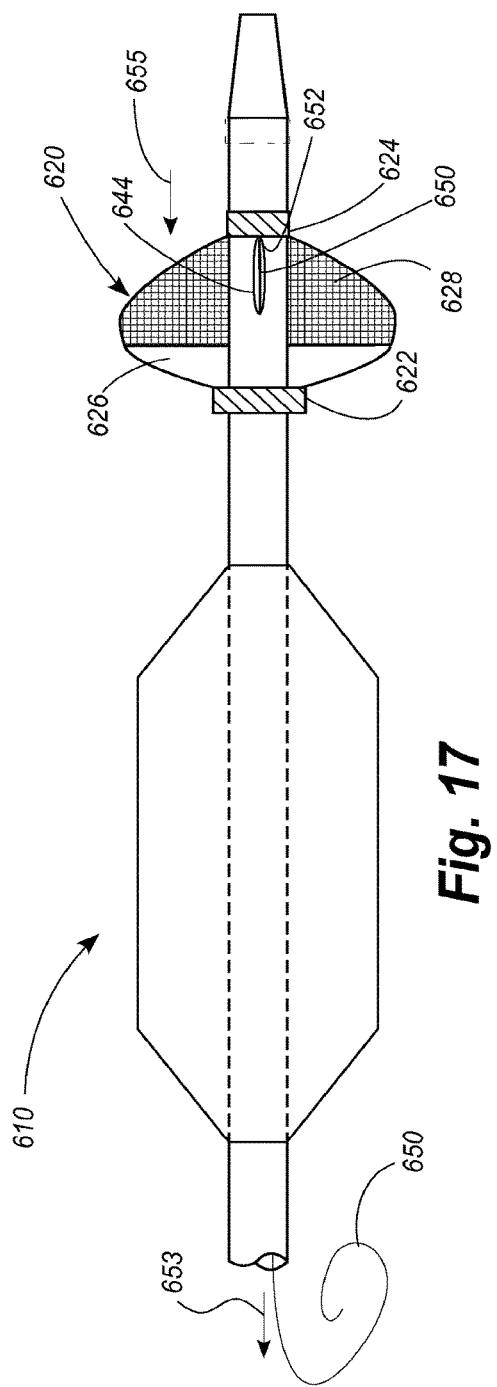

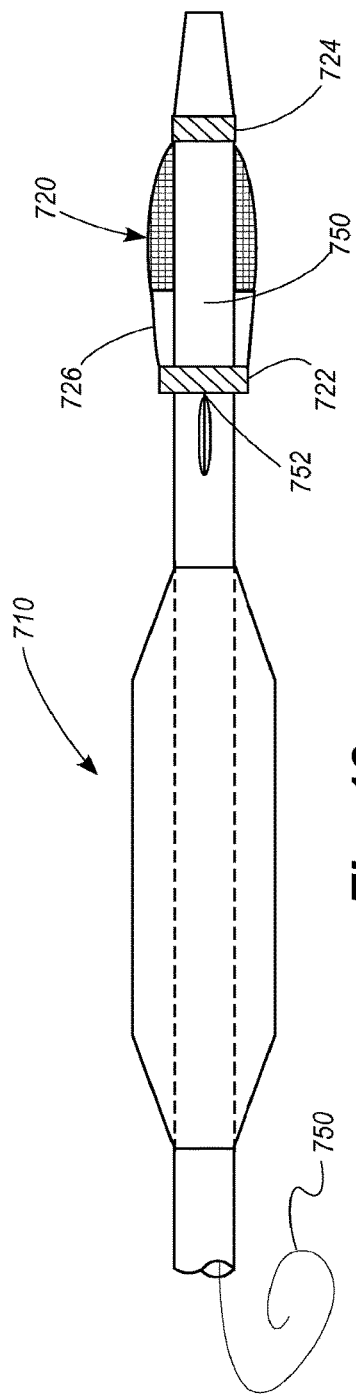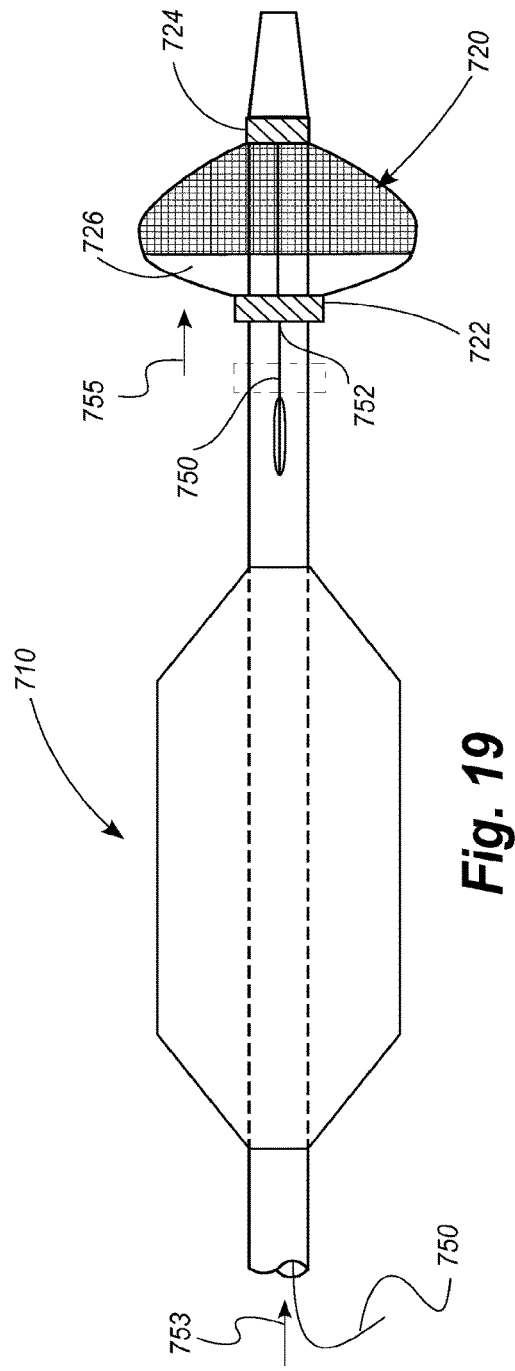
Fig. 18
Fig. 19

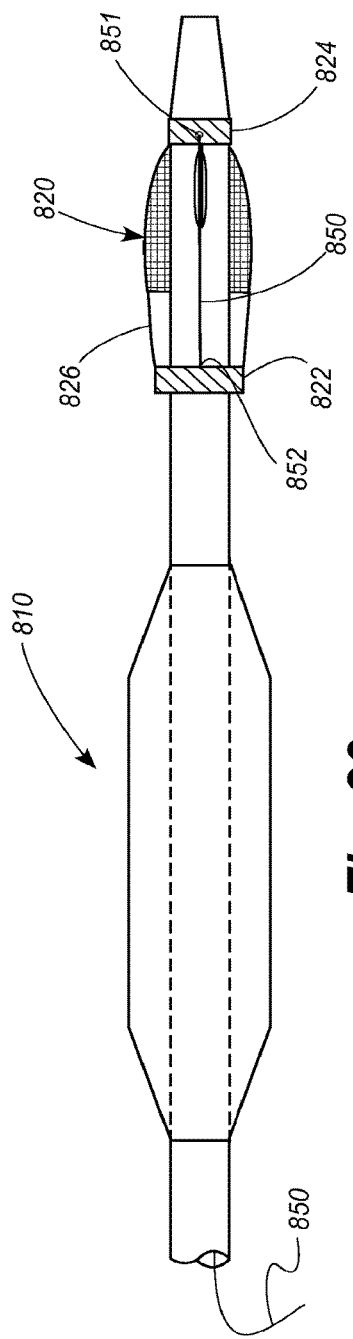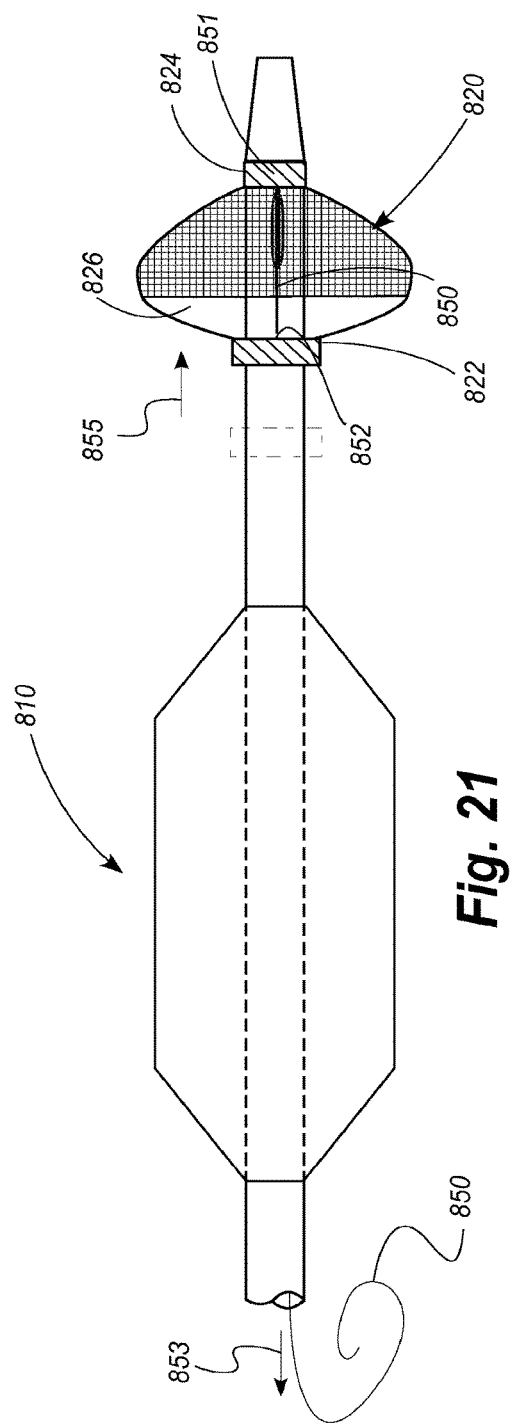

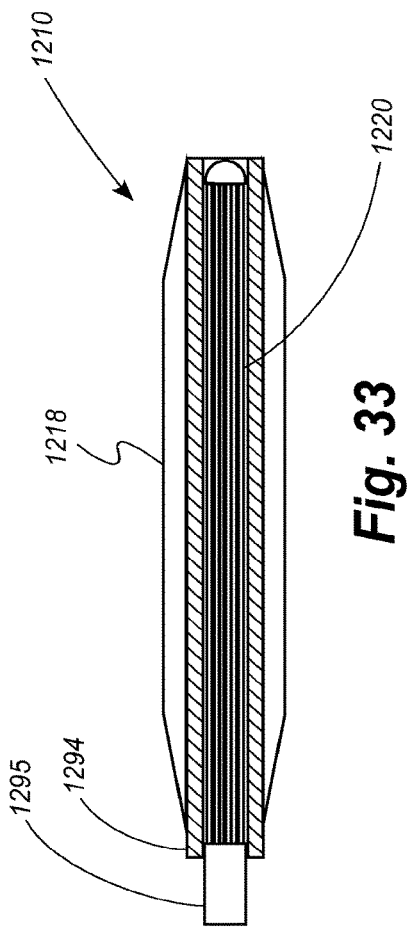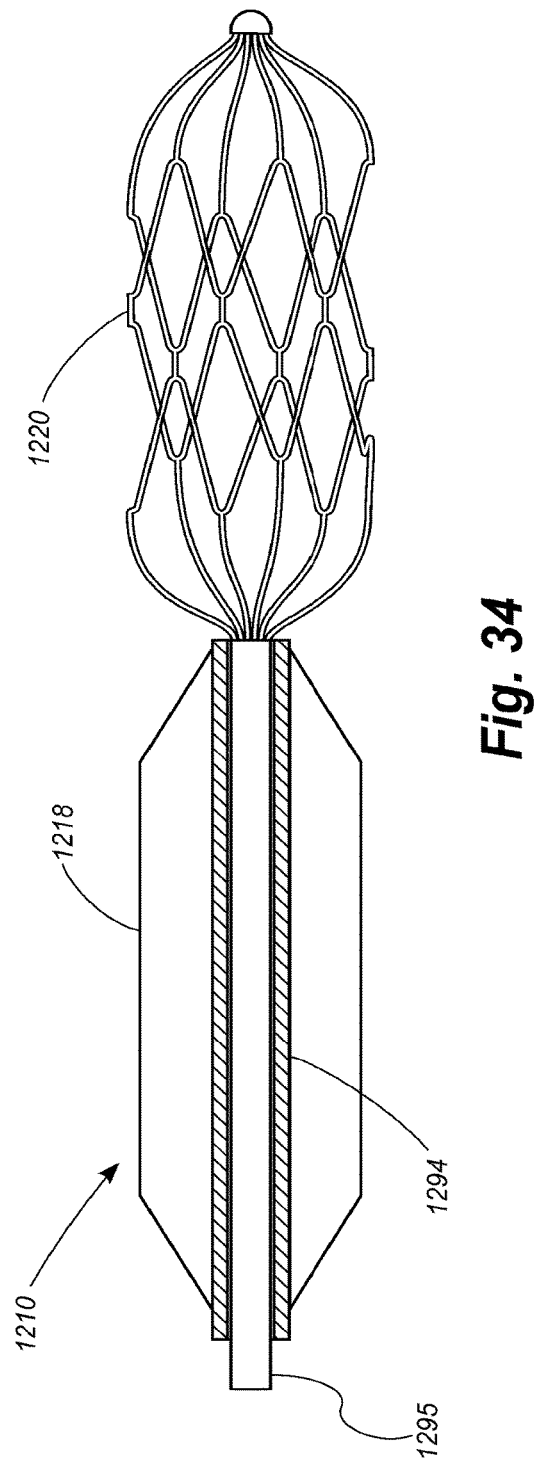

PERCUTANEOUS TRANSLUMINAL ANGIOPLASTY DEVICE WITH INTEGRAL EMBOLIC FILTER

CROSS-REFERENCE TO RELATED APPLICATION

This application is a continuation-in-part of U.S. patent application Ser. No. 10/997,803, filed Nov. 24, 2004, now U.S. Pat. No. 8,403,976. This application further claims priority to Provisional Patent Application No. 60/813,395, filed Jun. 14, 2006.

TECHNICAL FIELD

The present invention relates generally to surgical devices and relates more specifically to a percutaneous transluminal angioplasty device.

BACKGROUND OF THE INVENTION

The vascular bed supplies a constant flow of oxygen-rich blood to the organs. If plaque builds up in these vessels, blockages can develop, reducing blood flow to the organs and causing adverse clinical symptoms, up to and including fatality.

Angioplasty is a catheter-based procedure performed by a physician to open up a blocked vessel and restore blood flow. An entry site is opened, for example in the patient's groin, arm, or hand, and a guide wire and catheter are advanced under fluoroscopic guidance to the location of the blockage. A catheter having a small balloon adjacent its distal end is advanced under fluoroscopic guidance until the balloon lies within the stenosed region. The balloon is then inflated and deflated one or more times to expand the stenosed region of the artery.

Since diseased vessels are comprised of a range of material from early-stage thrombosis to late-stage calcified plaque, angioplasty can release embolic particles downstream from the stenosed location. These embolic particles can result in adverse clinical consequences. It has been shown that it is beneficial to trap these embolic particles to prevent them from traveling downstream with blood flow to the capillary bed (e.g., Bairn D S, Wahr D, George B, et al., Randomized Trial of a Distal Embolic Protection Device During Percutaneous Intervention of Saphenous Vein Aorto-Coronary Bypass Grafts, Circulation 2002; 105:1285-90).

In addition to balloon angioplasty, stenoses may also be treated with stents and with mechanical thrombectomy devices. These devices are also prone to releasing embolic particles downstream from the stenosed location.

There are systems available today that are used to catch these embolic particles. They are primarily filter systems or occlusion balloon systems built on a guidewire. These systems have shortcomings related to simplicity of use and crossing tight lesions with a filter or balloon guidewire that is larger in diameter than the guide wire which is normally used. These embolic protection guidewires also have flexibility and stability problems that make the protected angioplasty procedure difficult in many cases. In the case of saphenous vein grafts, the problems relate specifically to aorto-ostial lesions, where the guidewire may not be long enough to provide support, or distal vein graft lesions, where there is not enough of a landing zone for the filter. The latter is a problem as currently available filter systems have a considerable distance between the treatment balloon and the distal filter. This distance is a problem not only in distal vein graft lesions, but also in arterial stenoses in which there is a side branch immediately after the stenosis. In such cases, the filter can often be deployed only distal to the side branch, thus leaving the side branch unprotected from embolic particles.

SUMMARY OF THE INVENTION

Stated generally, the present invention comprises a percutaneous transluminal angioplasty device with integral embolic filter. Because the filter is integral with the catheter of the angioplasty device, there is no need to insert a separate device into the vessel. Further, proper placement of the angioplasty balloon assures proper placement of the embolic filter.

Stated somewhat more specifically, the percutaneous transluminal angioplasty device of the present invention comprises an embolic filter mounted to the catheter shaft at a location distal to the angioplasty balloon, stent, or mechanical thrombectomy device. Thus the filter is downstream from the blockage and is properly positioned to capture embolic particles that may be set loose into the blood stream as the angioplasty procedure is performed. The embolic filter is normally collapsed against the catheter shaft to facilitate introduction and withdrawal of the device to and from the operative site. Once the angioplasty balloon, stent, or mechanical thrombectomy device is properly positioned, however, means operatively associated with the embolic filter are actuated to erect the filter to position a filter mesh across the lumen of the coronary artery.

In some embodiments the means for erecting the filter comprises a balloon which longitudinally displaces one end of the filter toward the other, causing longitudinal ribs to bow outward, thus erecting the filter mesh. In other embodiments the means for erecting the filter comprises a balloon interposed within the proximal and distal ends of the filter, whereby inflating the balloon will bias the ribs away from the catheter shaft, causing the ribs to bow outwardly to erect the filter mesh. In still other embodiments the means for erecting the filter comprises a pull wire attached to one end of the filter, such that pulling on the wire longitudinally displaces one end of the filter toward the other, causing longitudinal ribs to bow outward, thus erecting the filter mesh.

In one embodiment of the invention, a reservoir is provided at the distal tip of the filter so that when the device collapses for withdrawal, debris does not get pushed out of the filter.

Objects, features, and advantages of the present invention will become apparent upon reading the following specification, when taken in conjunction with the drawings and the appended claims.

BRIEF DESCRIPTION OF THE DRAWINGS

FIG. 6 is a second embodiment of a percutaneous transluminal angioplasty device according to the present invention, which differs from the percutaneous transluminal angioplasty of FIGS. 1 and 2 in that the actuation balloon is on the proximal side of the embolic filter, and the filter erects from a different direction.

FIG. 7 is a view of the percutaneous transluminal angioplasty device of FIG. 6 showing the angioplasty balloon inflated and the embolic filter erected.

FIG. 8 is a third embodiment of a percutaneous transluminal angioplasty device and differs from the previously described embodiments in that the means for erecting the embolic filter is a bellows. FIG. 8 shows the angioplasty balloon and the embolic filter in their collapsed positions.

FIG. 9 is another view of the percutaneous transluminal angioplasty device of FIG. 8 showing the angioplasty balloon and the embolic filter in their inflated or raised positions.

FIG. 10 is another embodiment of a percutaneous transluminal angioplasty device according to the present invention which employs a bellows to raise and lower the embolic filter. The embodiment of FIG. 10 differs from the embodiment of FIGS. 8 and 9 in that the bellows is disposed on the distal end of the filter such that the filter opens from the opposite direction. FIG. 10 shows the angioplasty balloon and the embolic filter in their deflated or collapsed positions.

FIG. 11 is another view of the percutaneous transluminal angioplasty device of FIG. 10, showing the angioplasty balloon inflated and the embolic filter raised.

FIG. 12 shows still another embodiment of a percutaneous transluminal angioplasty device according to the present invention, in which the balloon interposed between the catheter shaft and the ribs forces the ribs upward, thereby causing them to bow into the erected embolic filter. FIG. 12 shows the device with the angioplasty balloon and the embolic filter in their collapsed or lowered positions.

FIG. 13 is another view of the percutaneous transluminal angioplasty device of FIG. 12, showing the angioplasty balloon in its inflated condition and the embolic filter in its erected condition.

FIG. 14 is another embodiment of a percutaneous transluminal angioplasty device according to the present invention. This embodiment differs from the embodiments of FIGS. 12 and 13 in that the balloon is located at the opposite end of the filter. Nonetheless, when inflated, the balloon forces the ribs away from the shaft and into their accurate positions, thereby raising the embolic filter. FIG. 14 shows the embodiment with the angioplasty balloon collapsed and the embolic filter retracted against the catheter shaft.

FIG. 15 is another view of the embodiment of FIG. 14, showing the angioplasty balloon inflated and the embolic filter erected.

FIG. 16 is still another embodiment of a percutaneous transluminal angioplasty device according to the present invention. This embodiment employs a pull wire operable from outside the patient which is attached to a front ring of the embolic filter. When the physician exerts tension on the wire, the distal ring is displaced proximally, bringing it closer to the proximal ring, thereby causing the ribs to bow outward and thereby erecting the embolic mesh filter. FIG. 16 shows the device with the angioplasty balloon deflated and the embolic filter collapsed against the catheter shaft.

FIG. 17 is a different view of the embodiment of FIG. 16 and shows the angioplasty balloon inflated and the embolic filter erected.

FIG. 18 is another embodiment of a percutaneous transluminal angioplasty device according to the present invention, showing the angioplasty balloon and the embolic filter in their collapsed conditions.

FIG. 19 is another view of the embodiment of FIG. 18, showing the angioplasty balloon inflated and the embolic filter raised.

FIG. 20 is yet another embodiment of a percutaneous transluminal angioplasty device according to the present invention, showing the angioplasty balloon and the embolic filter in their collapsed conditions.

FIG. 21 is another view of the embodiment of FIG. 20, showing the angioplasty balloon inflated and the embolic filter raised.

FIG. 33 is a side cutaway view of another embodiment of an angioplasty device showing an angioplasty balloon in its deflated condition and an embolic filter in a retracted state.

FIG. 34 is a side cutaway view of the angioplasty device of FIG. 33 showing the angioplasty balloon inflated and the embolic filter erected.

DETAILED DESCRIPTION OF THE DISCLOSED EMBODIMENTS

Figure 1:
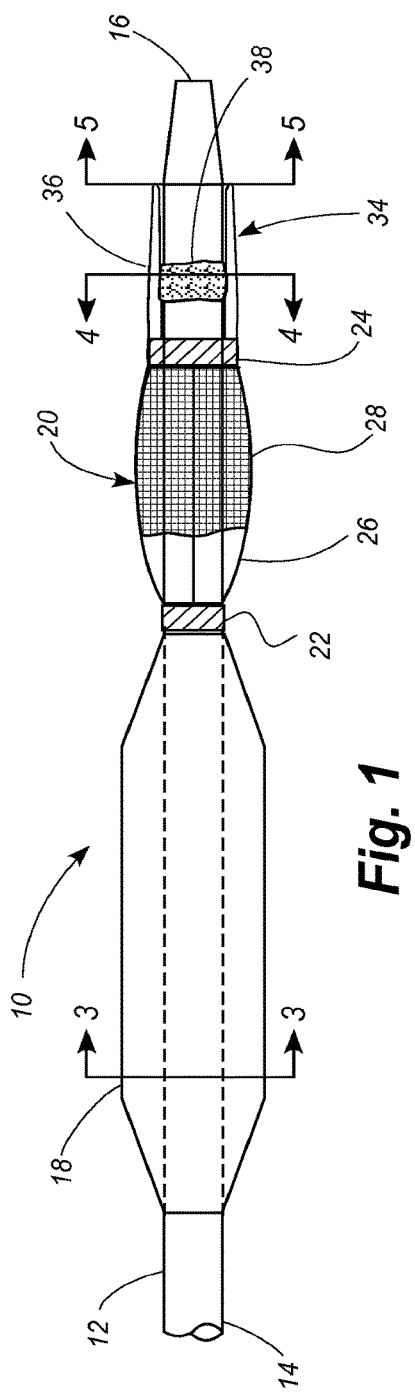
FIG. 1 is a partial cut away side view of first embodiment of a percutaneous transluminal angioplasty device according to a first embodiment of the disclosed invention, with the angioplasty balloon and embolism filter in their collapsed positions.
Figure 2:
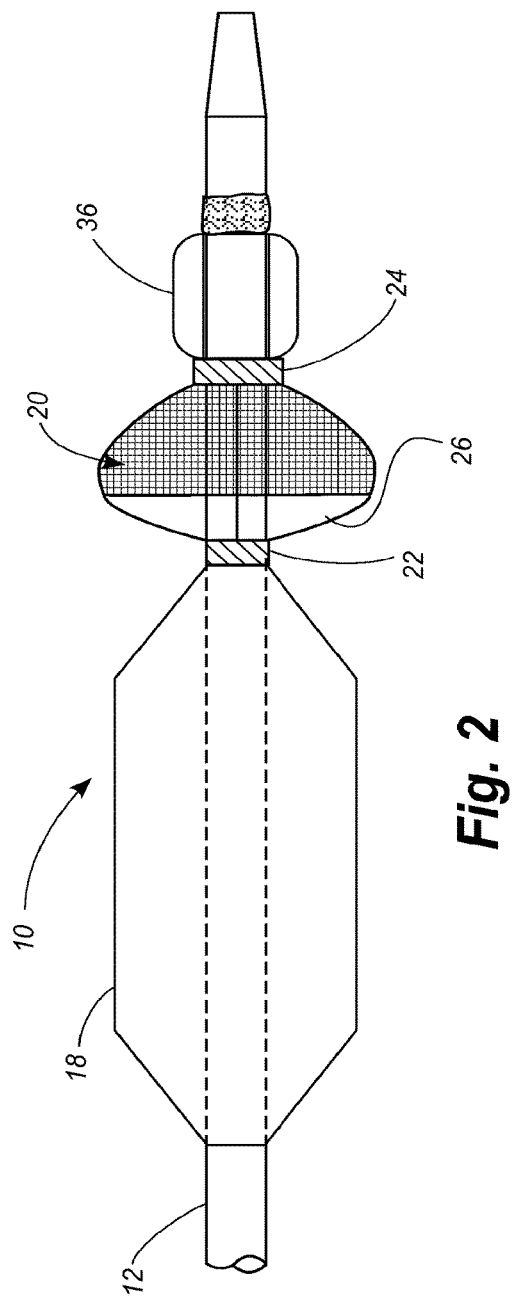
FIG. 2 is a partial cut away side view of the percutaneous transluminal angioplasty device of FIG. 1 showing the angioplasty balloon and embolism filter in their erected positions.

Referring now to the drawings, in which identical numbers indicate identical elements throughout the various views, FIGS. 1 and 2 illustrate a first embodiment of a percutaneous transluminal angioplasty device 10 according to the present invention. The device 10 comprises an elongated catheter 12 having a shaft 14 with a proximal end (not shown) and a distal end 16. Spaced a short distance proximally from the distal end 16 of the catheter 12 is an angioplasty balloon 18 of conventional design. In FIG. 1 the angioplasty balloon 18 is shown in a deflated or collapsed condition. In FIG. 2 the angioplasty balloon 18 is shown in an inflated condition.

Located between the angioplasty balloon 18 and the distal tip 14 of the catheter 12 is a collapsible filter 20. The filter 20 includes a proximal ring portion 22 and a distal ring portion 24. A plurality of elongated ribs 26 extend generally longitudinally between the proximal and distal rings 22, 24. These ribs can be made of a shape memory material, such as nitinol, and in their baseline position, these ribs are collapsed. A filter mesh 28 overlies the distal portion of the ribs 26. In the embodiment of FIGS. 1 and 2, the distal ring 24 is movable toward and away from the proximal ring 22. As the distal ring 24 moves toward the proximal ring 22, the ribs 26 bow outward. As the ribs 26 bow outward, the filter mesh 28 overlaying the ribs is erected. FIG. 1 shows the filter 20 in its collapsed condition, while FIG. 2 shows the filter in its erected condition.

Means 34 are included for erecting and collapsing the filter 20 of the device 10 shown in FIGS. 1 and 2. Specifically a balloon 36 has its distal end 38 bonded to the shaft 14 of the catheter 12. When the distal ring 24 is in its withdrawn position, as shown in FIG. 1, the bulk of the balloon 36 is folded forward over the shaft 14 of the catheter 12. When the balloon 36 is inflated, as shown in FIG. 2, the balloon 36 expands proximally, pushing the distal ring 24 in a proximal direction, causing the ribs 26 to bow outward and thereby erecting the filter 20. When the balloon 32 is deflated, the shape memory ribs straighten, urging the distal ring 24 in a distal direction and collapsing the filter 20 close to the shaft 14 of the catheter 12.

Figure 3:
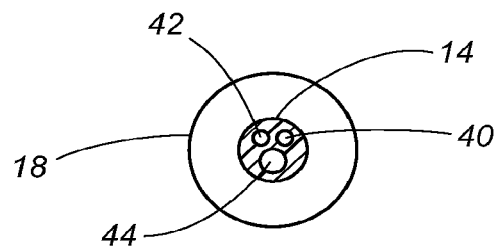
FIG. 3 is a cross sectional view taken along line 3-3 of FIG. 1.
Figure 4:
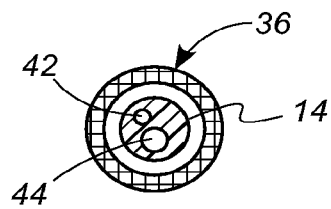
FIG. 4 is a cross sectional view taken along line 4-4 of FIG. 1.
Figure 5:
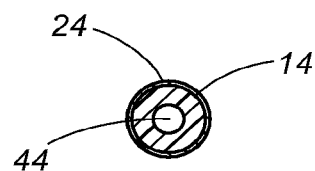
FIG. 5 is a cross sectional view taken along line 5-5 of FIG. 1.

FIGS. 3, 4, and 5 show cross sections of the device 10 at various locations along its length. Referring first to FIG. 3, the catheter shaft 12 has three lumens: two smaller lumens and a large main lumen. The two smaller lumens are inflation lumens, one lumen 40 for the angioplasty balloon 18, and one lumen 42 for the balloon 36 which controls the filter 20. The larger main lumen 44 is used to receive a guide wire (not shown) over which the device 10 is advanced to position the device for performing an angioplasty procedure.

Referring now to FIG. 4, this cross section is taken at a location distal to the angioplasty balloon 18. Consequently, the angioplasty balloon inflation lumen 40 has terminated and is no longer visible. Thus, FIG. 4 shows only two lumens, the main lumen 44 for receiving the guide wire, and the smaller inflation lumen 42 for the filter balloon 36.

Referring now to FIG. 5, this cross section is taken at a location distal to the filter balloon 36, and hence only the main lumen 44 is visible.

FIGS. 6 and 7 show an alternate embodiment of a percutaneous transluminal angioplasty device 110 according to the present invention. This device is similar to the device 10 previously described, with the exception that the filter 120, in this case, has its distal ring 124 fixed, and the proximal ring 122 of the filter 120 is movable toward and away from the distal ring to cause the ribs 126 to bow outwardly or to straighten. The balloon 136 is located on the proximal side of the filter 120 and pushes the proximal ring 122 in a distal direction when the balloon 136 is inflated.

Referring now to FIGS. 8 and 9, yet another alternate embodiment of a percutaneous transluminal angioplasty device 210 is shown. This device is similar to the device shown in FIGS. 1 and 2, with the exception that the means for erecting the filter 220 is a bellows 236, instead of a balloon. In FIG. 8, the bellows 236 is uninflated and hence it is in a collapsed condition, permitting the ribs 226 of the filter 220 to straighten out against the shaft 214 of the catheter 212. In FIG. 9, the bellows 236 has been inflated, pushing the proximal ring 222 in a distal direction, bowing out the ribs 236 and erecting the filter mesh 238.

FIGS. 10 and 11 illustrate still another embodiment of a percutaneous transluminal angioplasty device 310. This device is similar to the device shown in FIGS. 8 and 9, with the exception that the bellows 336 is placed on the distal side of the filter 320. Thus, when the bellows 336 is inflated, it moves the distal ring 324 in a proximal direction toward the proximal ring 322, thereby causing the ribs 326 to bow outwardly, erecting the filter mesh 338.

FIGS. 12 and 13 depict another embodiment of a percutaneous transluminal angioplasty device 410. In this device the means for erecting the filter comprises a balloon 436 disposed between the catheter shaft 414 and the ribs 426 adjacent the fixed distal ring 424 of the filter 420. When the balloon 436 is inflated, it forces the ribs 426 outward away from the catheter shaft 414, thereby bowing the ribs and drawing the proximal ring 422 of the filter 420 in a distal direction. As the ribs 426 bow outward, the filter mesh 428 is erected, thereby raising the filter 420.

FIGS. 14 and 15 show a device 510 similar to that shown in FIGS. 12 and 13, with the exception that the balloon 536 is placed between the catheter shaft 512 and the ribs 526 adjacent the proximal ring 522 of the filter 520. In the device 510, the distal ring 524 is free to slide along the catheter shaft 512, such that when the balloon 536 is inflated and forces the ribs 526 to bow outward, the distal ring 524 slides in a proximal direction, as indicated by the arrow 539 as shown in FIG. 15, permitting the filter 520 to raise.

The embodiment 610 shown in FIGS. 16 and 17 employs a different means for erecting the filter 620. In the embodiment 610 a pull wire 650 is used. The pull wire 650 extends through what would formerly have been used as the filter balloon inflation lumen 644, and the distal end 652 of the pull wire 650 is attached to the distal ring 624. When the physician wishes to raise the filter 620, he exerts a tension on the wire 650, as indicated by the arrow 653, thus drawing the distal ring 624 in a proximal direction as indicated by the arrow 655 toward the proximal ring 622. The ribs bow 626 outward, erecting the filter mesh 628 as shown in FIG. 17.

In the device 710 shown in FIGS. 18 and 19, the distal end 752 of a push wire 750 is attached to the proximal ring 722. Thus when the wire 750 is pushed in the direction indicated by the arrow 753, the proximal ring 722 is advanced distally toward the distal ring 724 in the direction indicated by the arrow 755, causing the ribs 726 to bow outward and thereby erecting the filter 720, as shown in FIG. 19.

The device 810 shown in FIGS. 20 and 21 uses a pull wire 850 to erect the filter 820. The pull wire 850 wraps around an opening 851 in the stationary distal ring 824 and extends rearward toward the proximal ring 822 to which the distal end 852 of the pull wire is attached. Thus when tension is exerted on the pull wire 850 in the direction indicated by the arrow 853, the proximal ring 822 is drawn distally toward the distal ring 824 in the direction indicated by the arrow 855, causing the ribs 826 to bow outward and thereby erecting the filter 820, as shown in FIG. 21.

Figure 22:
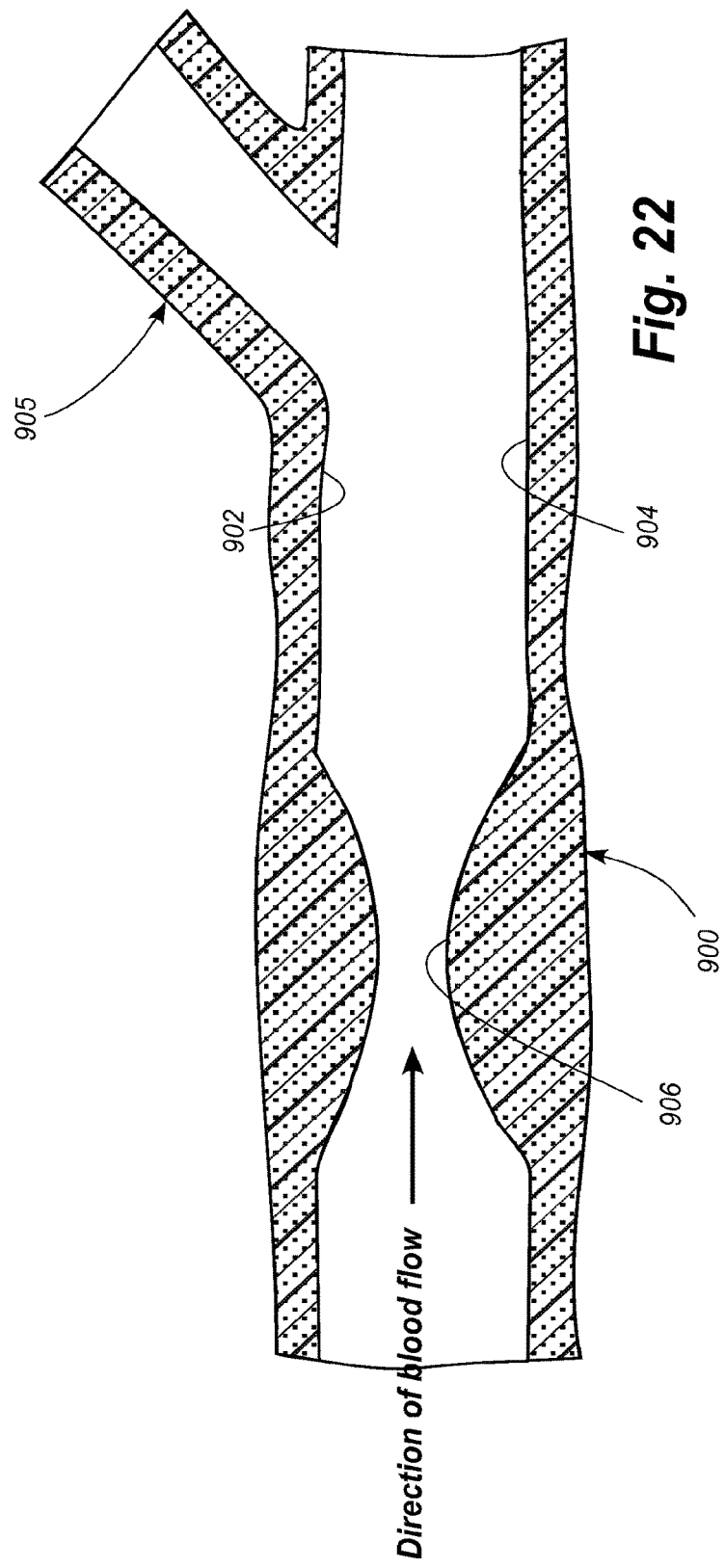
FIG. 22 shows a side cut away view of a coronary artery with a stenosis.

The operation of the device 10 will now be explained with respect to FIGS. 22-25, and it will be understood that the other devices operate on a substantially the same principles. FIG. 22 shows a vascular structure (e.g., coronary artery, saphenous vein graft, renal artery, carotid artery, superficial femoral artery, etc.) 900 with upper and lower walls 902, 904, a branch vessel 905, and a stenosis or blockage 906 caused by the build up of plaque or other substances on the arterial walls in such a way as to narrow the diameter of the arterial lumen, and in the process, constrict the flow of blood therethrough.

Figure 23:
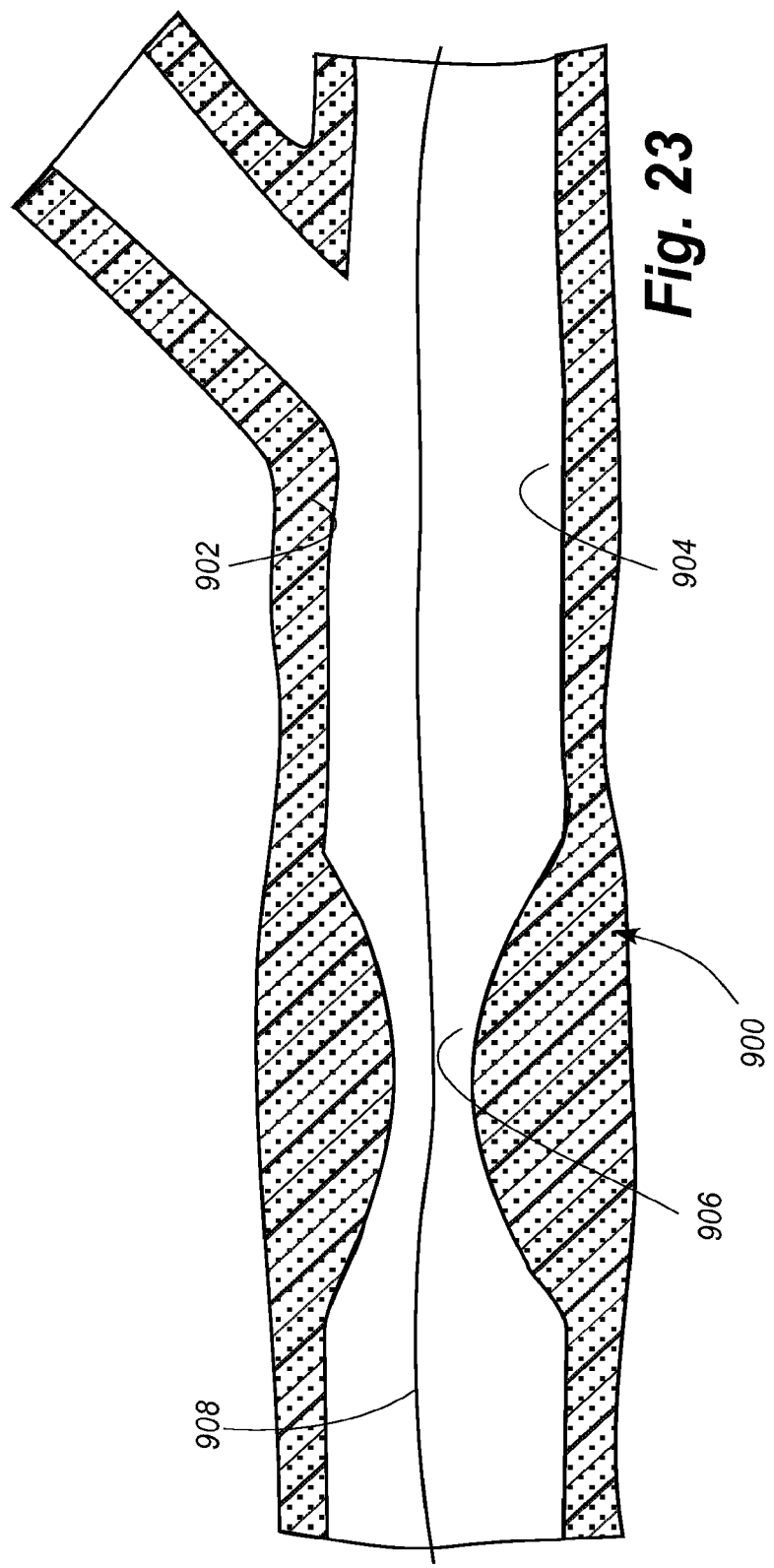
FIG. 23 shows the coronary artery of FIG. 20 with a guide wire fed through the coronary artery and through the stenosis.

In FIG. 23, a guide wire 908 has been inserted by the physician, such as through the femoral artery, and guided through the vascular system until the guide wire passes through the stenosis 906 in the vascular structure 900.

Figure 24:
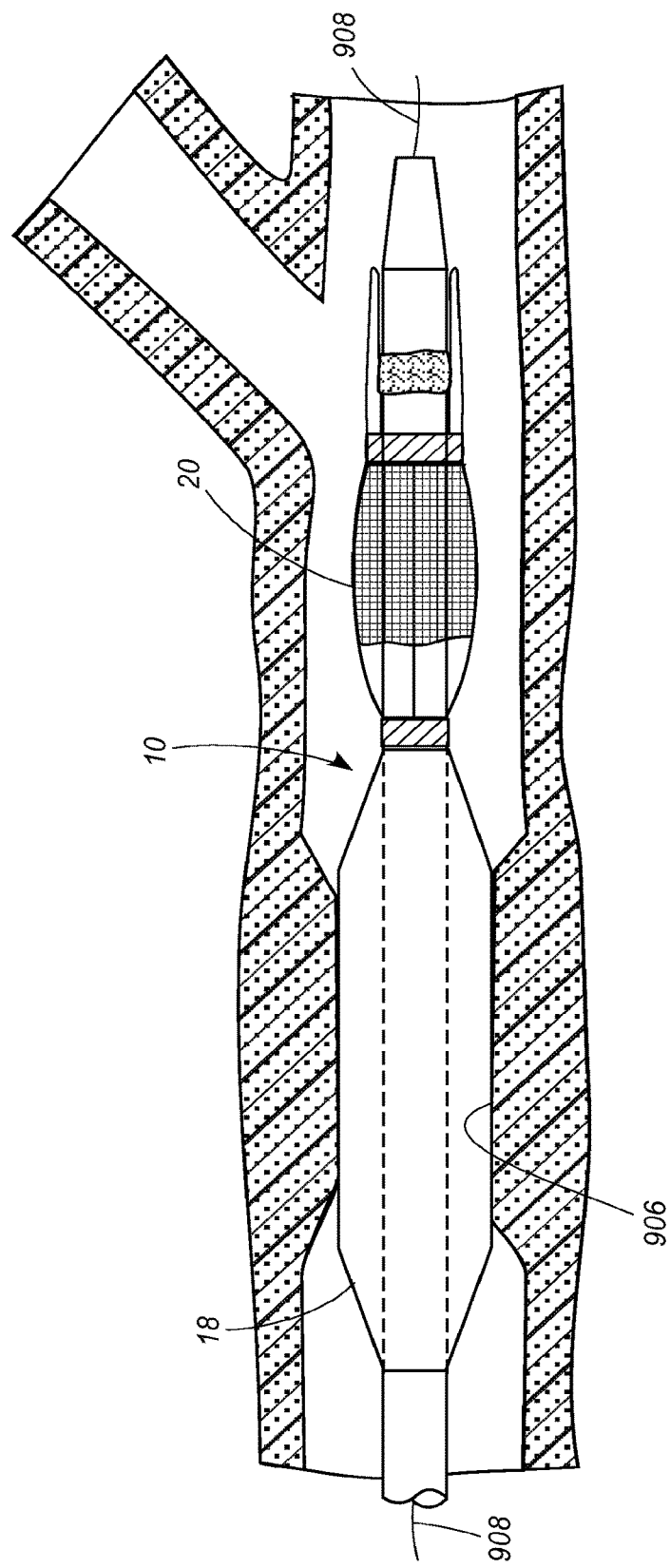
FIG. 24 shows the device of FIG. 1 threaded over the guide wire of FIG. 23 and positioned such that the angioplasty balloon is located within the stenosis.

Referring now to FIG. 24, the apparatus 10 has been inserted over the guide wire 908 and advanced to a location wherein the angioplasty balloon resides within the stenosis 906. The embolic filter 20 resides a few centimeters distal or downstream from the angioplasty location. In FIG. 24 both the angioplasty balloon and the embolic filter are shown in their collapsed conditions.

Figure 25:
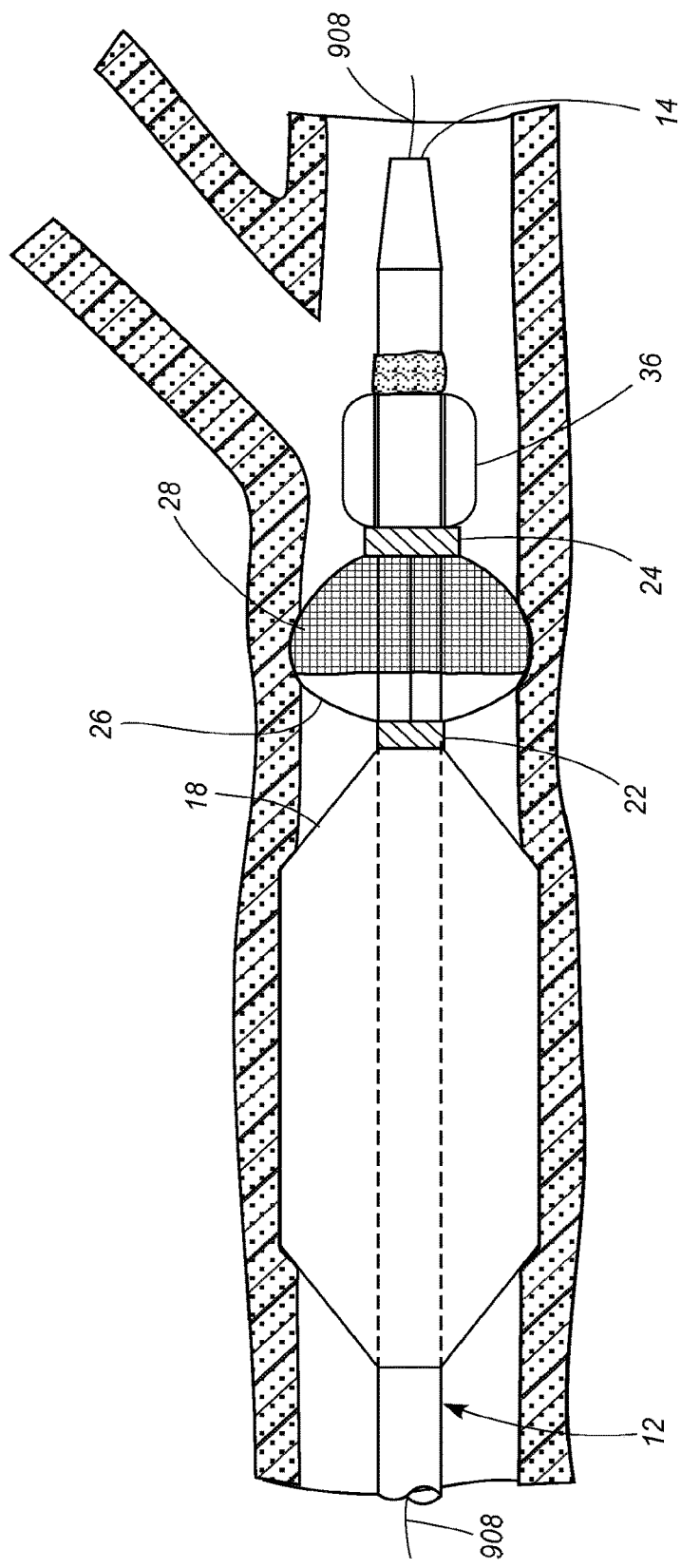
FIG. 25 illustrates the angioplasty balloon in its inflated condition to reduce the stenosis, and the embolic filter has been erected to capture any embolic particles that may break loose into the blood stream as a result of the angioplasty procedure.

In FIG. 25 the embolic filter 20 has been erected by inflating the filter balloon 36, causing the distal ring 22 to slide in a proximal direction along the catheter shaft 12. As the ribs 26 bow outward, the mesh filter material 28 supported by the ribs spreads so as to cover substantially the entire arterial lumen. The angioplasty balloon 18 is now inflated. As the balloon 18 inflates, it pushes tissue and plaque forming the stenosis 906 outward, opening the stenosis and possibly loosening embolic particles in the process. Any such embolic particles which get captured in the blood stream will be caught by the embolic filter 20 and will thereby be prevented from traveling to a location where they can cause clinical damage.

Of interest in FIG. 25 is the close proximity in which the filter 20 is erected relative to the stenosis 906. Despite the short "landing area" between the stenosis 906 and the branch vessel 905, the filter 20 is erected to capture embolic particles upstream of the branch vessel.

When removing the device 10 from the coronary artery, the preferred procedure is to deflate the angioplasty balloon 18 first, prior to collapsing the embolic filter 20. In this way, any embolic particles that are broken loose as the angioplasty balloon 18 deflates will be captured by the filter 20. The embolic filter balloon 20 is then deflated, permitting the ribs 26 and filter mesh 28 to collapse against the shaft 14 of the catheter 12. Any embolic particles captured by the mesh 28 are trapped against the shaft 14. The device 10 is then withdrawn over the guide wire 908 and removed from the patient's body.

Figure 26:
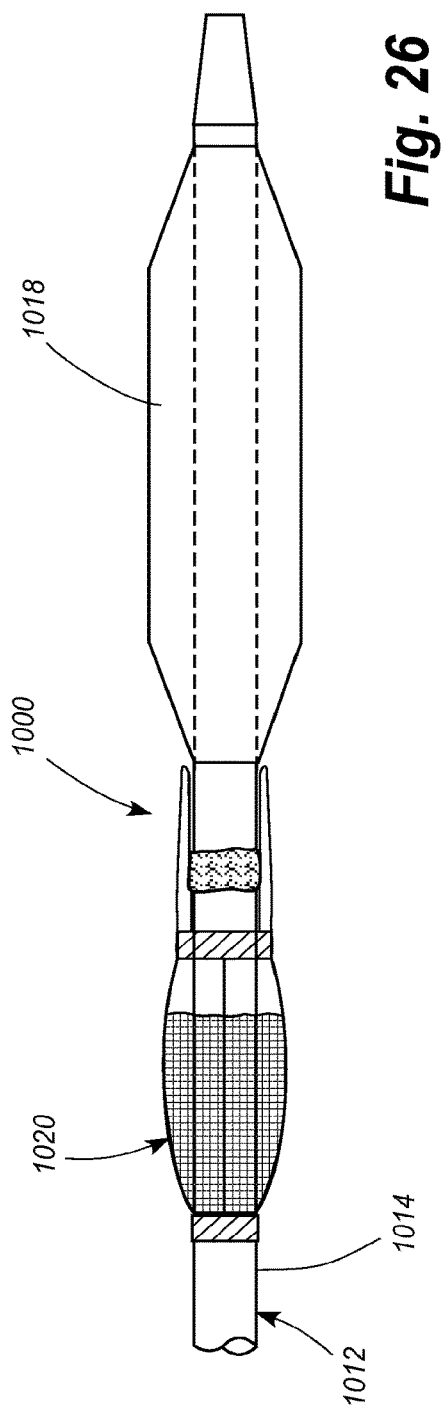
FIG. 26 is a partial cut away side view of an embodiment of a device in which the angioplasty balloon and embolism filter, shown in their collapsed positions, are reversed on the catheter shaft for peripheral vascular applications in which blood flows in the opposite direction.
Figure 27:
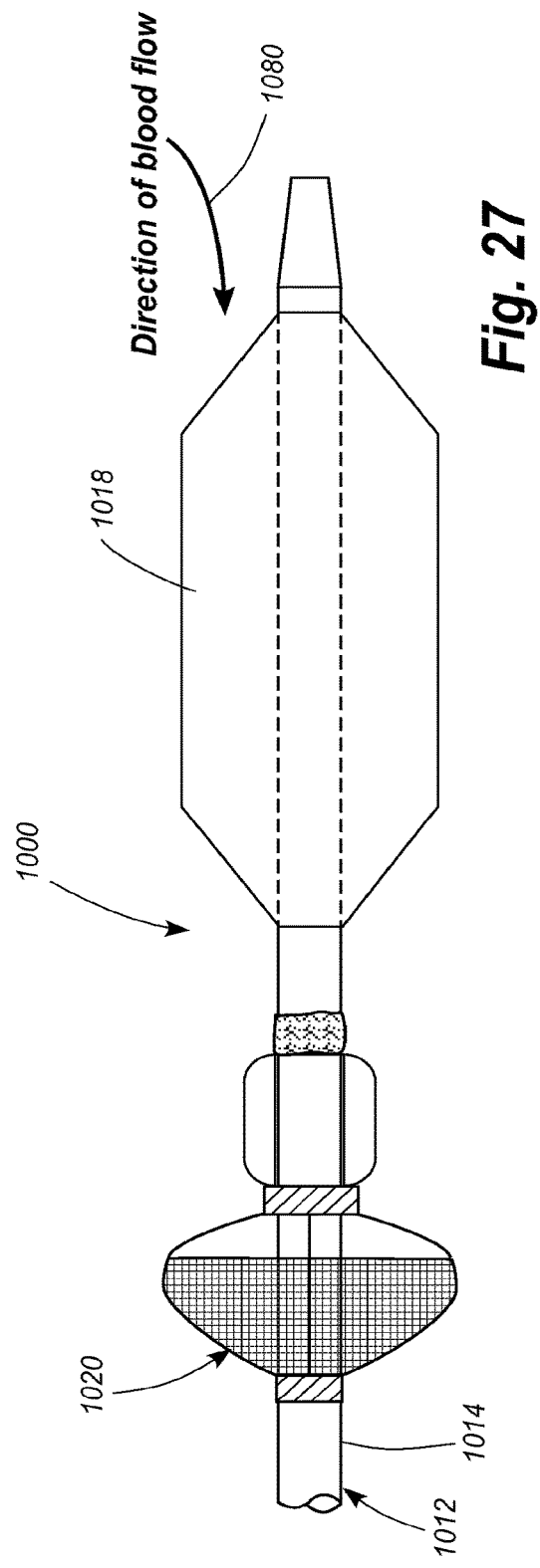
FIG. 27 is a partial cut away side view of the device of FIG. 26 showing the angioplasty balloon and embolism filter in their erected positions.

In various peripheral vascular applications, it may be necessary to insert the catheter against the direction of blood flow (e.g., the aorta). FIGS. 26 and 27 illustrate a device 1000 in which the angioplasty balloon 1018 and the embolic filter 1020 are reversed on the shaft 1014 of the catheter 1012. Thus with the blood flowing within the vessel in the direction indicated by the arrow 1080, the embolic filter 1020 will be proximal to the angioplasty balloon 1018 and thus positioned to capture any embolic particles that may be dislodged by the angioplasty balloon.

While the embodiment 1000 of FIGS. 26 and 27 employs the same method and device for erecting the embolic filter as the embodiment 10 of FIGS. 1-3, it will be understood that the methods and devices for erecting the embolic filter of other embodiments disclosed above are equally applicable to a configuration like the device of embodiment 1000 where the angioplasty balloon is positioned between the embolic filter and the tip of the device.

Figure 28:
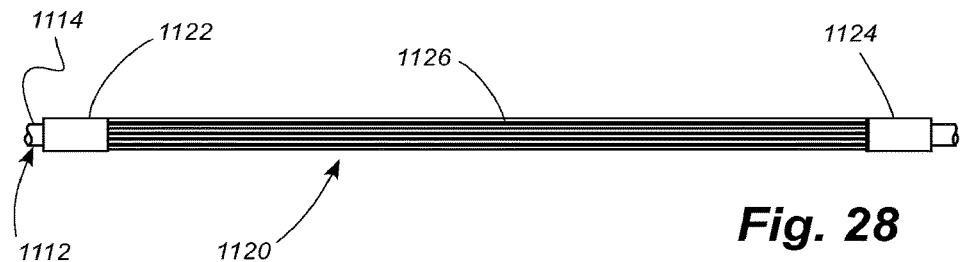
FIG. 28 is a side view of an embolism filter according to another embodiment of the present invention.
Figure 29:
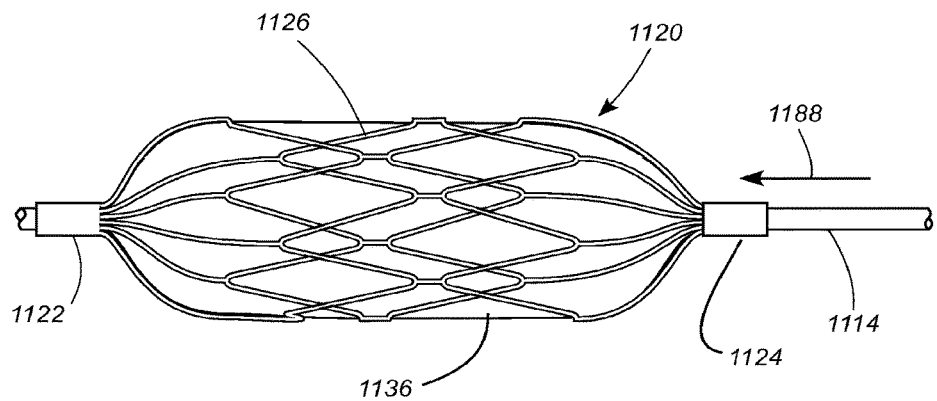
FIG. 29 is a side view of the embolism filter of FIG. 28 with the inflation balloon expanded to erect the embolism filter; filter mesh is shown removed to reveal interior detail.
Figure 30:
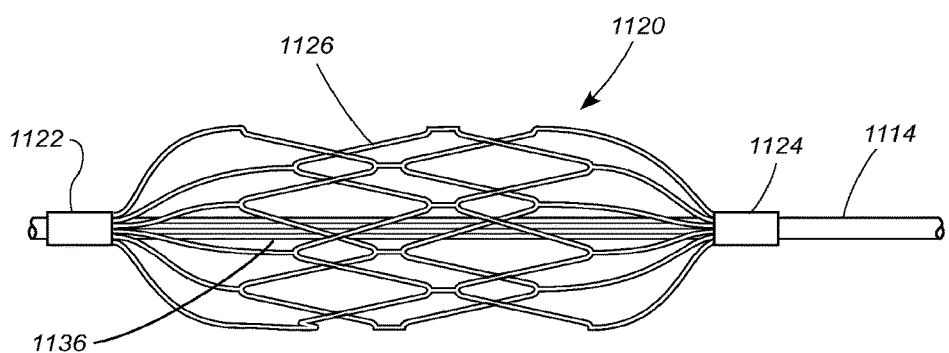
FIG. 30 is a side view of the embolism filter of FIG. 28 with the inflation balloon deflated; filter mesh is shown removed to reveal interior detail.
Figure 31:
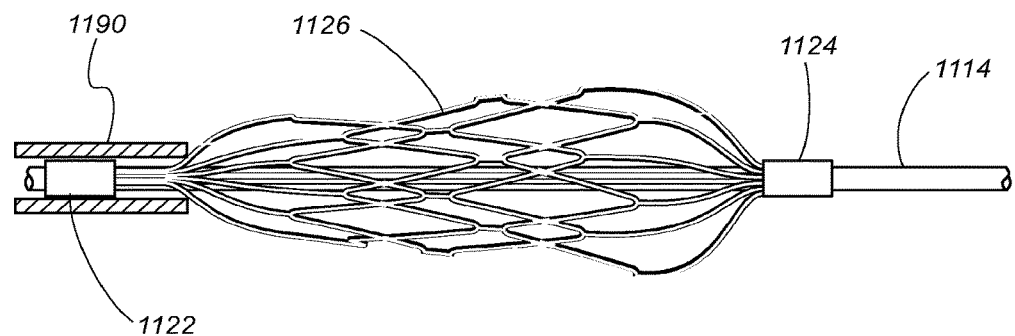
FIG. 31 is a side view of the embolism filter of FIG. 28 being retracted into the forward end of a catheter to collapse the filter; filter mesh is shown removed to reveal interior detail.

FIGS. 28-32 show still another embodiment of an embolic filter 1120 for use in conjunction with an angioplasty balloon. FIGS. 28-32 show only the embolic filter 1120 and not the angioplasty balloon, but it will be understood that the embolic filter is located on the same catheter 1114 as the angioplasty balloon in the same manner as the embodiments previously disclosed. Further, FIGS. 29-31 show the embolic filter 1120 without its filter mesh 1128 for clarity of illustration.

In FIG. 28 the embolic filter 1120 is folded closely against the shaft 1114 of the catheter 1112. The ribs 1126 of the filter 1120 extend between a proximal ring portion 1122 and a distal ring portion 1124. The distal ring portion 1124 is slidably mounted on the shaft 1114 of the catheter 1112, and the proximal ring portion 1122 is fixed with relation to the shaft of the catheter. In FIG. 29 the embolic filter balloon 1136 has been inflated, expanding the ribs 1126 of the embolic filter. As the ribs expand, the distal ring portion 1124 slides in the proximal direction, as shown by the arrow 1188. Once expanded, the ribs 1126 maintain their shape, such that when the embolic filter balloon 1136 is deflated, as shown in FIG. 30, the embolic filter 1120 remains expanded.

To retract the embolic filter 1120, a second, outer catheter 1190 is advanced over the catheter 1112, as shown in FIG. 31, causing the ribs 1126 to collapse as the embolic filter is withdrawn into the forward end of the outer catheter 1190. As the ribs 1126 collapse, the distal ring portion 1124 slides in the distal direction. Once the embolic filter 1120 has been completely retracted into the forward end of the outer catheter 1190, the outer and inner catheters are withdrawn simultaneously.

Figure 32:
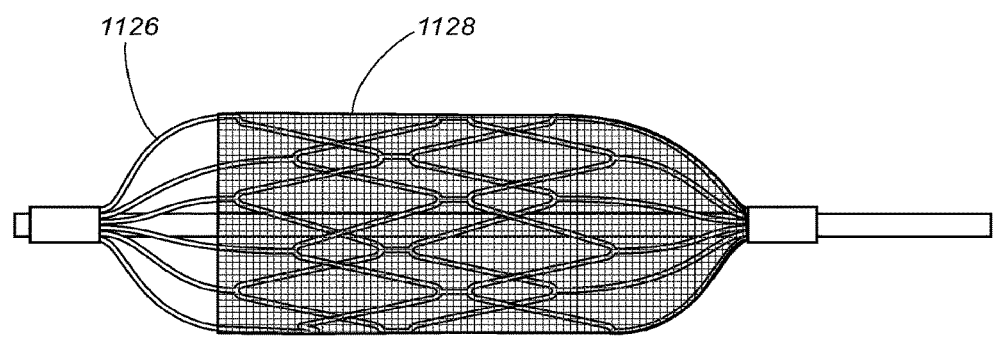
FIG. 32 is a side view of the embolism filter of FIG. 28, with the filter expanded and filter mesh in place.

FIG. 32 shows the embolic filter 1120 with filter mesh 1128 positioned over the ribs 1126.

FIGS. 33 and 34 illustrate a further embodiment of a percutaneous angioplasty device 1210, in which the embolic filter 1220 is located on a different carrier than the angioplasty balloon 1218. Specifically, the angioplasty balloon 1218 is located on an outer catheter 1294, and the embolic filter 1220 is located at the forward end of an inner catheter 1295. (The embolic filter 1220 is shown without filter mesh in FIGS. 33 and 34 for clarity of illustration.) The outer catheter preferably has three lumens, one for inflating the angioplasty balloon 1218, one for accommodating a guide wire (not shown), and one for receiving the inner catheter 1295 and embolic filter 1220. The inner catheter 1295 is slidably telescopically disposed within the outer catheter 1294. The ribs 1226 of the embolic filter 1220 are formed from a shape-memory metal such as nitinol and are constructed to normally assume an "open" configuration. When retracted within the forward end of the outer catheter 1294, the ribs 1226 of the embolic filter collapse.

To use the percutaneous angioplasty device 1210, the inner catheter is inserted into the outer catheter so that the embolic filter 1220 is collapsed within the distal end of the device, as shown in FIG. 33. The outer and inner catheters 1294, 1295 are inserted together, such as through the femoral artery, over a guidewire and advanced through the vascular system to a location wherein the uninflated angioplasty balloon 1218 resides within the stenosis. Once location of the angioplasty balloon 1218 within the stenosis has been verified by suitable medical imaging technology, the inner catheter is advanced to progress the embolic filter 1220 beyond the forward end of the outer catheter 1294. As the embolic filter 1220 is freed from the confines of the outer catheter 1294, the ribs assume their expanded configuration and erect the embolic filter. Thereafter the angioplasty balloon 1218 may be inflated to treat the stenosis, and any emboli loosened during the procedure will be captured by the embolic filter 1220 downstream of the stenosis.

When the angioplasty procedure has been completed, the angioplasty balloon 1218 is deflated, and the embolic filter 1220 is withdrawn back into the forward end of the outer catheter 1294. The outer and inner catheters 1294, 1295 are then withdrawn together from the patient.

In the foregoing embodiment a wire can be substituted for the inner catheter 1295 as a means for carrying the embolic filter 1220.

Figure 35:
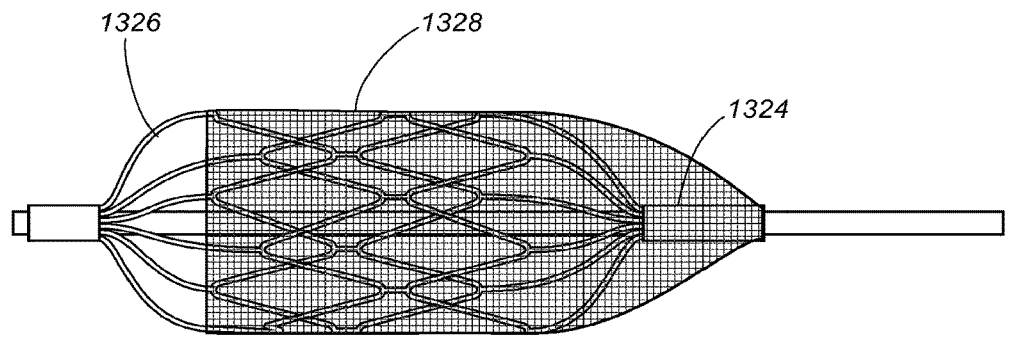
FIG. 35 is a side view of a further embodiment of an angioplasty device in which the filter mesh extends beyond the end of the ribs so as to form a sac when the filter is collapsed.
Figure 36:
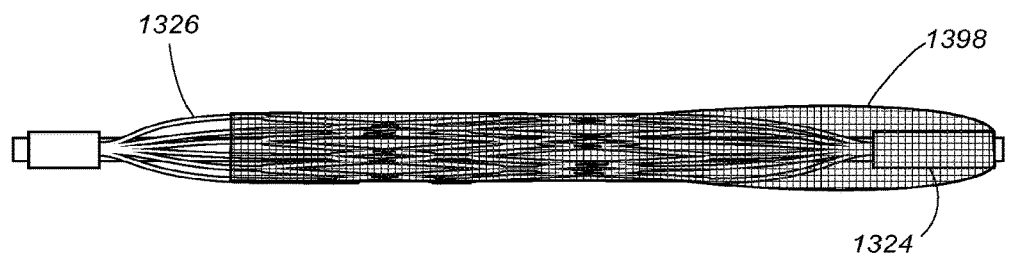
FIG. 36 is a side view of the embodiment of FIG. 35 showing the filter in a collapsed condition.

FIGS. 35 and 36 show an angioplasty device 1310 that is identical to the device 10, with the exception that the filter mesh 1328 extends distally beyond the end of the ribs 1326 and is attached to the distal end of the distal ring 1324. When the filter 1320 is collapsed, as shown in FIG. 36, a sac 1398 is formed which helps contain the embolic particles, thereby minimizing the possibility that the ribs 1326 will squeeze the particles out of the filter.

Figure 37:
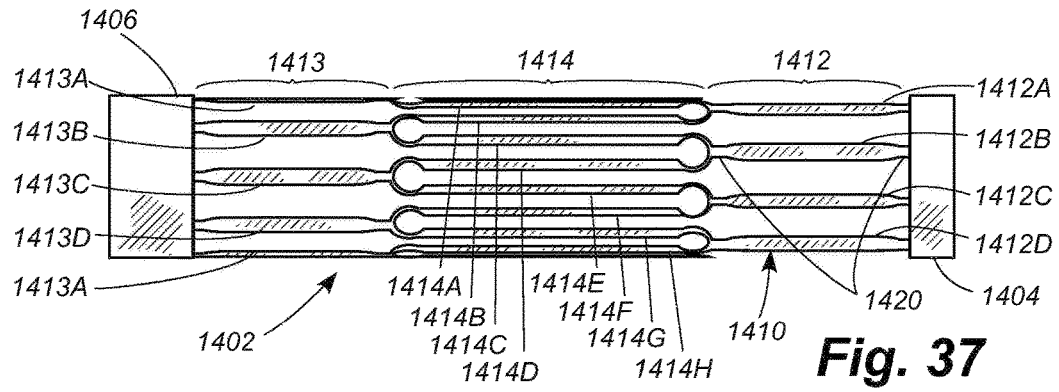
FIG. 37 is a projection of a generally cylindrical filter frame of a still further embodiment of a catheter with integral embolic filter, i.e., the generally cylindrical filter frame is shown unrolled and flattened.
Figure 38:
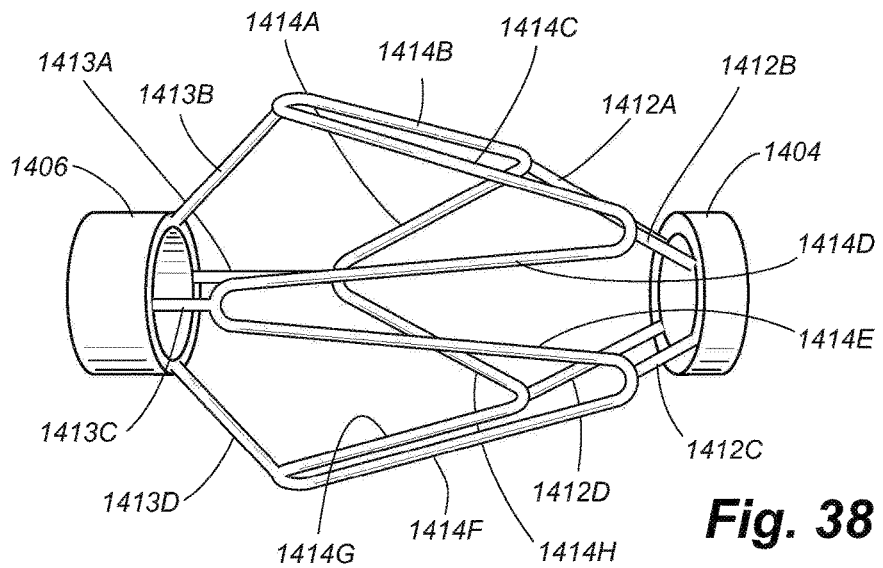
FIG. 38 is a perspective view of the filter frame of FIG. 37 showing the frame in an expanded condition.
Figure 39:
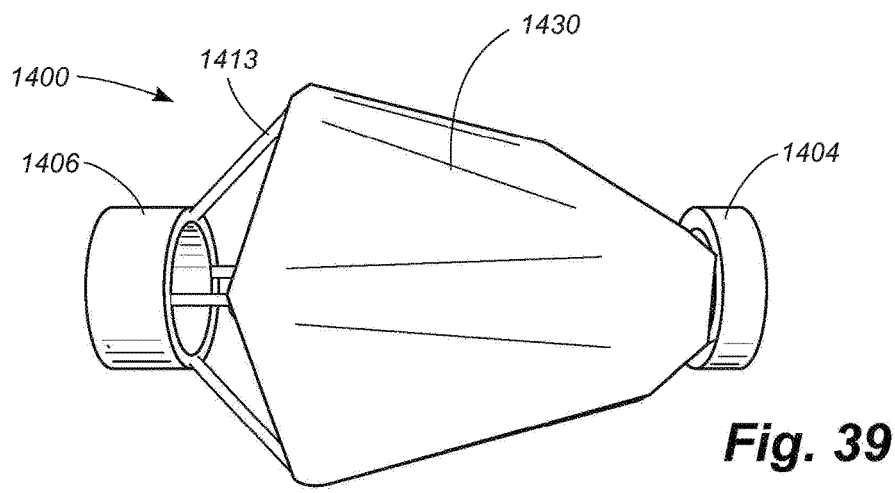
FIG. 39 is a perspective view of the expanded filter frame of FIG. 38 showing a filter membrane installed over the frame.

Referring now to FIGS. 37-39, an alternate embodiment of a filter 1400 is shown. The filter 1400 has a generally tubular shape with a proximal ring 1404 at one end, a distal ring 1406 at the other, and a filter frame 1402 connecting the two rings. FIG. 37 is a projection of a cylinder, i.e. a generally cylindrical filter 1400 is shown unrolled and flattened. The frame 1402 is made of flexible material such as Nitinol.

More specifically, the frame 1402 comprises a first plurality of longitudinal struts 1412 extending inward from one end ring 1404. A second plurality of longitudinal struts 1413 extends inward from the opposite end ring 1406. The second struts 1413 are circumferentially offset from the first struts 1412. A connecting plurality of intermediate struts 1414 link the adjacent ends of the longitudinal struts 1412, 1413. In the disclosed embodiment, the number of first longitudinal struts 1412 is equal to the number of second longitudinal struts 1413, and there are twice as many intermediate connecting struts 1414 as there are struts 1412 or struts 1413.

With further reference to FIG. 37, the end of first strut 1412A is connected to the ends of second struts 1413A and 1413B by intermediate struts 1414A and 1414B. The end of first strut 1412B is connected to the ends of second struts 1413B and 1413C by intermediate struts 1414C and 1414D. The end of first strut 1412C is connected to the ends of second struts 1413C and 1413D by intermediate struts 1414E and 1414F. The end of first strut 1412D is connected to the ends of second struts 1413D and 1413A by intermediate struts 1414G and 1414H. (Note that because FIG. 37 is a projection of a cylinder, i.e. a generally cylindrical filter unrolled and flattened, half of second strut 1413A is shown at the top of the projection, and the other half of second strut 1413A is shown at the bottom of the projection.)

In the disclosed embodiment the intermediate struts 1414 form a serpentine-like pattern. A first end of intermediate strut 1414A is connected to a first end of intermediate strut 1414B by a loop portion. A second end of intermediate strut 1414B is connected to a second end of intermediate strut 1414C by another loop portion, and so on. In the disclosed embodiment, the longitudinal struts 1412, 1413 are connected to the intermediate struts 1414 at the loop portions.

Points of weakness 1420 are formed on the support frame 1402 in strategic locations to facilitate controlled bending of the frame 1402. In the disclosed embodiment these points of weakness comprise points of reduced cross-sectional area. Further, in the disclosed embodiment these points of weakness are formed at the connection points between the rings 1404, 1406 and the longitudinal struts 1412, 1413 and at the connection between the longitudinal struts 1412, 1413 and intermediate struts 1414. Because of the narrow width at the connection points the longitudinal struts 1412, 1413 can flare open in the radial direction, while simultaneously expanding causing the intermediate struts 1414 to expand radially.

When the proximal and distal rings 1404, 1406 are brought toward one another, such as by any of the mechanisms hereinabove described, the filter frame 1402 assumes an expanded configuration as shown in FIG. 38. The longitudinal struts 1412A-D and 1413A-D pivot radially outward, while the intermediate struts 1414A-H spread apart to permit circumferential expansion of the support frame 1402.

With further reference to FIG. 38, first longitudinal strut 1412A is connected by intermediate struts 1414A, H to two second longitudinal struts 1413A, 1413B. First longitudinal strut 1412B is connected by intermediate struts 1414C, D to two second longitudinal struts 1413B, 1413C. First longitudinal strut 1412C is connected by intermediate struts 1414E, F to two second longitudinal struts 1413C, 1413D. And first longitudinal strut 1412D is connected by intermediate struts 1414G, H to two second longitudinal struts 1413D, 1413A. Thus each of the first longitudinal struts 1412A-D is connected to the ends of two corresponding second longitudinal struts 1413A-D by intermediate struts 1414A-H.

As further illustration that the second struts 1413A-D are circumferentially out of alignment with the first struts 1412A-D, FIG. 37 shows that the strut 1413B lies between intermediate struts 1414B and 1414C. In turn, intermediate struts 1414B and 1414C both lie between struts 1412A and 1412B. Strut 1413B thus lies between struts 1412A and 1412B such that the strut 1413B is circumferentially offset with respect to both struts 1412A and 1412B. This same logic can be applied to the remainder of the struts 1413 to illustrate that the struts 1413 are circumferentially offset with respect to the struts 1412 in a plane that is substantially perpendicular to the longitudinal axis of the catheter 12.

FIG. 39 shows the filter frame 1402 covered in a filter membrane 1430. The distal end of the filter membrane is open to permit embolic particles to enter the filter, where they are trapped by the filter membrane.

Figure 40:
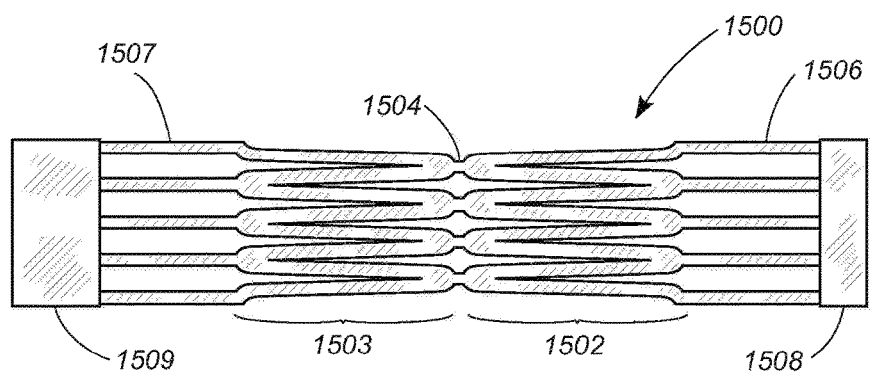
FIG. 40 is a projection of a generally cylindrical filter frame of yet another embodiment of a catheter with integral embolic filter, i.e., the generally cylindrical filter frame is shown unrolled and flattened.
Figure 41:
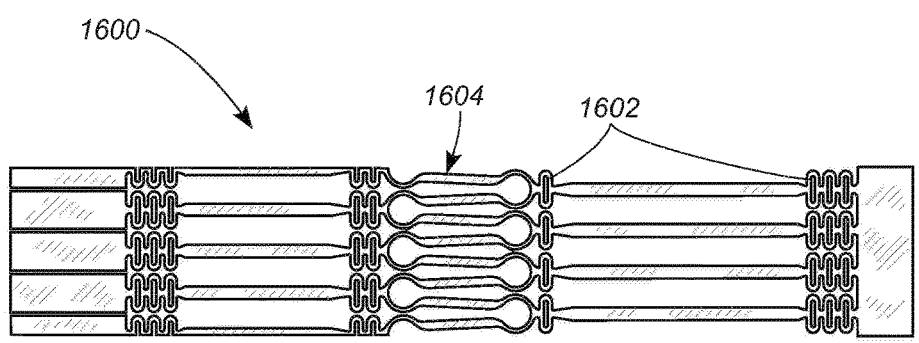
FIG. 41 is a projection of a generally cylindrical filter frame of still another embodiment of a catheter with integral embolic filter, i.e., the generally cylindrical filter frame is shown unrolled and flattened.

FIGS. 40 and 41 are cylindrical projections depicting alternate frame designs. In FIG. 40, the frame 1500 comprises two sets of intermediate struts 1502, 1053 that form serpentine patterns, and two sets of longitudinal frame members 1506, 1507 interconnecting the intermediate struts and the rings 1508, 1509. The two sets of intermediate struts 1502, 1503 are joined by connecting members 1504. Points of weakness are formed at strategic locations, e.g. at connections between longitudinal struts 1506, 1507 and intermediate struts 1502, 1503 and at the connections between the intermediate struts 1502, 1503 and the connecting members 1504.

FIG. 41 depicts another embodiment of a frame 1600 in which the points of weakness are formed by circular or oval cutouts 1602 transverse to the longitudinal axis of the struts 1604. These type of structures 1602 provide flexibility resulting in easier opening and closing of the frame 1600. These structures 1604 also reduce the stress induced permanent set and hence, allow the frame 1600 to retract back to its original shape. The oval and/or circular structures 1602 also provide enough longitudinal rigidity which will force the filter frame to open.

Figure 42:
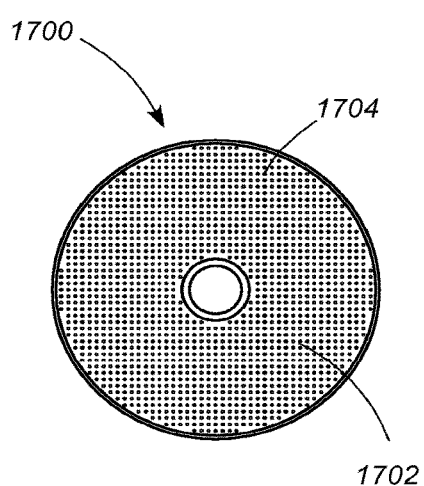
FIG. 42 is an end view of a filter membrane of a type suitable for use with the filter frames of FIGS. 37, 40, and 41.
Figure 43:
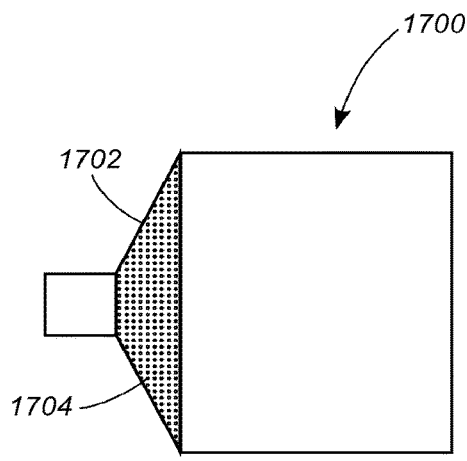
FIG. 43 is a side view of the filter membrane of FIG. 42.
Figure 44:
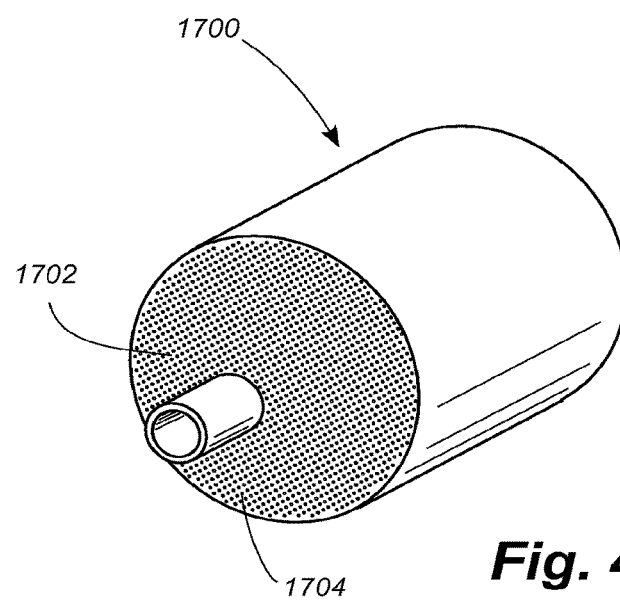
FIG. 44 is an isometric view of the filter membrane of FIG. 42.

FIGS. 42-44 illustrate an embodiment of a filter membrane 1700. The filter membrane 1700 is in the shape of a funnel. The conical surface 1702 of the funnel has a plurality of holes 1704 formed therein. The filter membrane 1700 is comprised of semi-compliant material such as nylon or PebaxT or could be made up of elastic materials such as thermoplastic elastomers or thermoset elastomers. Some examples of thermoset elastomers polyurethane and copolymers (Pellathane™ T Ecothane™, Chronofles™, etc). These materials allow placement of the holes 1704 close to each other. In the disclosed embodiment, the size of the holes 1704 is 40 microns, and the holes 1704 are placed 40 microns apart.

The filter membrane 1700 is attached to a support frame, such as the frames 1400, 1500, or 1600 hereinabove described, such that it covers one end of the frame as well as the centrally located serpentine strut structure. The other set of longitudinal struts remain exposed. The filter membrane 1700 may be attached on the outside of the frame or on the inside of the frame. In addition, the proximal end of the membrane can be terminated at the proximal ring or can extend beyond the ring to attach to the shaft of the catheter.

The filters herein depicted are deployed by pulling or pushing an actuation wire or inflating an actuation balloon, depending on the type of catheter chassis being used. As the filter is erected the serpentine struts expand circumferentially. The filter membrane is then deployed. Upon removal of the actuation force the filter retracts to its normally closed position.

An advantage of the filter material is that its natural shape is in a closed or collapsed condition. The filter material stretches as the filter is erected and collapses to its normal condition when the frame is retracted. Therefore, the membrane has no permanent set during storage and can always be expanded to a correct size. Further, because the filter collapses under the resiliency of the filter material, the filter does not require a recovery sheath. If needed, however, a sheath may be used to further collapse the filter with embolic debris prior to retrieval Preferably, but not necessarily, the filters of the disclosed embodiment are characterized by a long filter body that opposes the vessel wall over a greater area, thus reducing the chance of leakage between the filter and the vessel wall.

In each of the foregoing examples, it will be appreciated that an angioplasty balloon is but one means for relieving a stenosis in a vessel. Stents, mechanical thrombectomy devices, or other suitable apparatus may be substituted for the angioplasty balloon and positioned on the catheter at a location proximal to the embolic filter. Thus any emboli loosened by the stent or mechanical thrombectomy device will be captured by the embolic filter in the same manner as described above with respect to the angioplasty balloon.

While the foregoing disclosed embodiments comprise filter ribs of a shape memory metal such as nitinol, it will be appreciated that similar results can be obtained by using any suitable resilient material. The ribs would be formed straight, forced open by the balloon, and return to their normal shape as a result of the resiliency of the structure. Or, in the case of the embodiment of FIGS. 33 and 34, the ribs would be initially formed in an open position, deformed inwardly to fit within the outer catheter, and return to their normal open position when released from the confines of the outer catheter.

Variations in the design of the filter are also contemplated. For example, while both ends of the ribs 26 of the filter 20 are mounted to rings 22, 24, it will be appreciated that the ends of the ribs at the fixed end of the filter can be secured directly to the catheter shaft.

It will be appreciated that the present invention permits the placement of the embolic filter very close to the means for treating the stenosis. This has the effect of minimizing the "landing area" of the filter and also permits the protection of side branches, as shown in FIGS. 22-25.

Finally, it will be understood that the foregoing embodiments have been disclosed by way of example, and that other modifications may occur to those killed in the art without departing from the scope and spirit of the appended claims.

What is claimed is:

1. A percutaneous interventional treatment apparatus comprising:
   an elongated catheter having a lumen, a proximal end portion, a distal end portion, an outer side wall, and a longitudinal axis;
   an interventional device operably coupled to the distal end portion of the elongated catheter;
   a filter operably coupled to the distal end portion of the elongated catheter and spaced from the interventional device relative to the longitudinal axis of the elongated catheter, wherein the filter is selectively collapsible and expandable about and between a collapsed position and a deployed position, and wherein the filter comprises:
      a movable ring slidably coupled to the elongated catheter;
      a fixed ring spaced from the movable ring relative to the longitudinal axis of the elongated catheter and immovably coupled to the elongated catheter,
      a tubular frame formed of a shape memory material having a shape memory that urges the filter towards the collapsed position and comprising a first end coupled to the movable ring and an opposed second end coupled to the fixed ring, wherein the tubular frame further comprises;
      a first plurality of longitudinal struts, each strut of the first plurality of longitudinal struts comprising a first end coupled to the fixed ring, a second end extending toward the movable ring, and at least one oval cutout, wherein the major axis of the at least one oval cutout is oriented transverse to the longitudinal axis of the strut of the first plurality of longitudinal struts,
a second plurality of longitudinal struts, each strut of the second plurality of longitudinal struts having a first end coupled to the movable ring, a second end extending toward the fixed ring, and at least one oval cutout, wherein the major axis of the at least one oval cutout is oriented transverse to the longitudinal axis of the strut of the second plurality of longitudinal struts,
at plurality of intermediate struts positioned between the first and second plurality of longitudinal struts, wherein a first side of a selected intermediate strut is coupled to the second end of a selected strut of the first plurality of longitudinal struts, and wherein a second side of the selected intermediate strut is coupled to the second end of a selected strut of the second plurality of longitudinal struts, and
a filter membrane operably coupled to the tubular frame;
an actuator wire extending through the lumen of the elongated catheter and having proximal and distal ends,
wherein, when the filter is in the collapsed position, pulling on the proximal end of the actuator wire exerts a force on the movable ring in a direction relative to the longitudinal axis of the elongated catheter that moves the movable ring towards the fixed ring; and
wherein selective movement of the movable ring towards the fixed ring causes at least a portion of the tubular frame to expand radially, thereby selectively expanding the filter towards the deployed position.

2. The percutaneous interventional treatment apparatus of claim 1, wherein the plurality of intermediate struts define a serpentine-like pattern.

3. The percutaneous interventional treatment apparatus of claim 2, wherein the tubular frame further comprises a plurality of points of weakness, wherein the plurality of points of weakness comprise a plurality of regions of reduced cross-sectional area.

4. The percutaneous interventional treatment apparatus of claim 3, wherein each strut of the first plurality of longitudinal struts and the second plurality of longitudinal struts is coupled to the serpentine-like pattern at a respective connection point, and wherein at least one point of weakness of the plurality of points of weakness is formed at a connection point between one of the first plurality of longitudinal struts and the second plurality of longitudinal struts and the serpentine-like pattern.

5. The percutaneous interventional treatment apparatus of claim 3, wherein the first end of each of the first plurality of longitudinal struts is connected to the fixed ring at a first series of connection points, wherein the first end of each of the second plurality of longitudinal struts is connected to the movable ring at a second series of connection points, and wherein at least one point of weakness of the plurality of points of weakness is formed at a first or a second connection point.

6. The percutaneous interventional treatment apparatus of claim 1, wherein the longitudinal struts of the second plurality of longitudinal struts are circumferentially offset with respect to the longitudinal struts of the first plurality of longitudinal struts in a plane substantially perpendicular to the longitudinal axis of the elongated catheter.

7. The percutaneous interventional treatment apparatus of claim 1, wherein the filter membrane is selectively attached to the tubular frame.

8. The percutaneous interventional treatment apparatus of claim 7, wherein the filter membrane overlies at least a portion of the tubular frame.

9. The percutaneous interventional treatment apparatus of claim 7, wherein the filter membrane is elastic, wherein the filter membrane is stretched when the tubular frame is expanded, and wherein the elasticity of the filter membrane exerts a radially inward force that urges the tubular frame towards the collapsed position.

10. The percutaneous interventional treatment apparatus of claim 1, wherein the interventional device comprises an angioplasty balloon.

11. The percutaneous interventional treatment apparatus of claim 1, wherein the interventional device comprises a stent.

12. The percutaneous interventional treatment apparatus of claim 1, wherein the interventional device comprises a mechanical thrombectomy device.

13. The percutaneous interventional treatment apparatus of claim 1, wherein the shape memory material of the tubular frame comprises nitinol.

14. The percutaneous interventional treatment apparatus of claim 1, wherein, upon removal of the tension from the actuator wire, the tubular frame urges the movable ring away from the fixed ring relative to the longitudinal axis of the elongated catheter.

15. The percutaneous interventional treatment apparatus of claim 1, wherein a distal portion of the actuator wire comprises a bend, and the distal end of the actuator wire is coupled to the movable ring.

16. The percutaneous interventional treatment apparatus of claim 1, wherein the interventional device is located proximal to the filter relative to the longitudinal axis of the elongated catheter.

17. The percutaneous interventional treatment apparatus of claim 1, wherein the interventional device is located distal to the filter relative to the longitudinal axis of the elongated catheter.

18. The percutaneous interventional treatment apparatus of claim 1, wherein the at least one oval cutout of each strut of the first plurality of longitudinal struts is disposed proximate a connection point between a first side of an intermediate strut and the second end of the struts of the first plurality of longitudinal struts, and wherein the at least one oval cutout of each strut of the second plurality of longitudinal struts is disposed proximate a connection point between a second side of an intermediate strut and the second end of the struts of the second plurality of longitudinal struts.

19. The percutaneous interventional treatment apparatus of claim 18, wherein each strut of the first plurality of longitudinal struts comprises at least two oval cutouts, each strut of the second plurality of longitudinal struts comprises at least two oval cutouts, or each longitudinal strut of the first and second plurality of longitudinal struts comprises at least two oval cutouts.

* * * * *